(12) United States Patent
Basch et al.

(10) Patent No.: US 6,867,413 B2
(45) Date of Patent: Mar. 15, 2005

(54) HIGH-FLOW RATE, LOW-NOISE, GAS SAMPLING APPARATUS AND METHODS FOR COLLECTING AND DETECTING PARTICULATE IN A GAS

(75) Inventors: Lauren R. Basch, East Greenbush, NY (US); William E. Rogers, Troy, NY (US); Harvey Patashnick, Voorheesville, NY (US)

(73) Assignee: Rupprecht & Patashnick Company, Inc.

( * ) Notice: Subject to any disclaimer, the term of this patent is extended or adjusted under 35 U.S.C. 154(b) by 117 days.

(21) Appl. No.: 10/177,749

(22) Filed: Jun. 21, 2002

(65) Prior Publication Data

US 2003/0234366 A1 Dec. 25, 2003

(51) Int. Cl.[7] ................................................. G01T 1/00
(52) U.S. Cl. ...................................... 250/255; 250/304
(58) Field of Search ........................... 250/435, 432 R, 250/304, 255

(56) References Cited

U.S. PATENT DOCUMENTS

| | | | |
|---|---|---|---|
| 3,295,359 A | 1/1967 | Peck | 73/28 |
| 3,540,261 A | 11/1970 | Scoggins | 73/28 |
| 3,657,920 A | 4/1972 | Teel et al. | 73/28 |
| 4,277,682 A | 7/1981 | Madelaine et al. | 250/380 |
| 4,795,612 A | 1/1989 | Keller | 422/64 |
| 4,951,749 A | 8/1990 | Carroll | 166/264 |
| 5,468,968 A | 11/1995 | Bailey et al. | 250/435 |
| 5,552,610 A * | 9/1996 | McIsaac et al. | 250/435 |
| 5,553,507 A | 9/1996 | Basch et al. | 73/863.01 |
| 5,646,357 A | 7/1997 | Ogden et al. | 73/863.31 |
| 5,717,147 A | 2/1998 | Basch et al. | 73/863.23 |
| 5,834,628 A * | 11/1998 | Hunter et al. | 250/255 |
| 5,898,114 A | 4/1999 | Basch et al. | 73/863.23 |
| 5,915,268 A | 6/1999 | Linker et al. | 73/23.2 |
| 6,023,982 A | 2/2000 | Basch et al. | 73/863.25 |
| 6,138,521 A | 10/2000 | Basch et al. | 73/863.25 |
| 6,167,107 A | 12/2000 | Bates | 377/10 |
| 6,192,767 B1 | 2/2001 | Fiorina | 73/863.21 |
| 6,321,609 B1 | 11/2001 | Mengel et al. | 73/863.21 |
| 6,435,043 B1 | 8/2002 | Ferguson et al. | 73/863.22 |
| 2001/0029793 A1 | 10/2001 | Moler et al. | 73/863.22 |

FOREIGN PATENT DOCUMENTS

EP 0964241 A1 12/1999

* cited by examiner

*Primary Examiner*—Constantine Hannaher
(74) *Attorney, Agent, or Firm*—Heslin Rothenberg Farley & Mesiti P.C.

(57) ABSTRACT

A high-flow rate, low-noise, gas sampling apparatus for collecting particulate such as biological, chemical, and radioactive material from a gas on a collector such as an impaction collector includes a housing having an inlet and an outlet and a fan disposed within the housing for drawing the gas into the inlet, past the collector for sampling, and exhausting the gas through the outlet. The fan is operable to produce a flow of gas through the housing of greater than about 50 liters per minute with a noise level emitted from the apparatus being less than about 60 decibels. The apparatus may be configured as a compact, unobtrusive, portable, lightweight apparatus for use in various indoor or outdoor locations. The apparatus may also include a sensor for the detection of radioactive material collected on the collector, a processor for monitoring the sampling, and the apparatus may be linked to a communications network such as the Internet. Methods for collecting particulate from a gas are also enclosed.

30 Claims, 8 Drawing Sheets

HIGH-FLOW RATE, LOW-NOISE, GAS SAMPLING APPARATUS AND METHODS FOR COLLECTING AND DETECTING PARTICULATE IN A GAS

FIELD OF THE INVENTION

This invention relates generally to gas samplers, and more particularly to gas sampling apparatus and methods for collecting and detecting particulate in a gas.

BACKGROUND OF THE INVENTION

Conventional gas samplers for collecting particulate include a housing having a vacuum pump for drawing gas past a collector such as a filter paper, a glass fiber filter media, a filter cassette, and an activated carbon cartridge.

Limitations with such conventional gas samplers for collecting particulate include the vacuum pump generally producing a low flow rate of gas to be sampled, the filter becoming clogged, and the vacuum pump being noisy.

There is a need for further gas sampling apparatus and methods for collecting and detecting particulate in a gas.

SUMMARY OF THE INVENTION

The present invention provides, in a first aspect, a high-flow rate, low-noise, gas sampling apparatus for collecting particulate from a gas on a collector. The apparatus includes a housing, and a device disposed within the housing for drawing the gas into the housing, past the collector for sampling, and exhausting the gas from the housing. The device is operable to produce a flow of gas through the housing of greater than about 50 liters per minute with a noise level emitted from the apparatus of less than about 60 decibels.

The present invention provides, in a second aspect, a gas sampling apparatus for collecting particulate from a gas on a collector and detecting presence of radioactive material. The apparatus includes a housing, a device disposed within the housing for drawing the gas into the housing, past the collector for sampling, and exhausting the gas from the housing. A radioactivity sensor detects the presence of radioactive material on the collector.

The present invention provides, in a third aspect, a high-flow rate, low-noise gas sampling apparatus for collecting particulate from a gas on a collector and detecting presence of radioactive material. The apparatus includes a housing, a device disposed within the housing for drawing the gas into the housing, past the collector for sampling, and exhausting the gas from the housing. A radioactivity sensor detects the presence of radioactive material on the collector. The device is operable to produce a flow of gas through the housing of greater than about 50 liters per minute with a noise level emitted from the apparatus being less than about 60 decibels. A processor monitors the sampling, and a communications interface allows connecting the processor to a communications network.

The present invention provides, in a fourth aspect, a method for collecting particulate from a gas in which the method includes drawing the gas into a housing, collecting particulate on a collector for sampling, discharging the gas from the housing, and wherein a flow rate of the gas through the housing is greater than about 50 liters per minute with a noise level emitted from the housing being less than about 60 decibels.

The present invention provides, in a fifth aspect, a method for collecting particulate from a gas and detecting presence of radioactive material in which the method includes drawing the gas into a housing, collecting particulate on a collector for sampling, detecting for the presence of radioactive material on the collector, and discharging the gas from the housing.

The present invention provides, in an sixth aspect, a method for collecting particulate from a gas and detecting presence of radioactive material in which the method includes drawing the gas into a housing, collecting particulate on a collector for sampling, detecting for the presence of radioactive material on the collector, discharging the gas from the housing, monitoring the sampling, communicating the monitoring of the sampling over a communications network, and wherein a flow rate of the gas through the housing is greater than about 50 liters per minute with a noise level emitted from the housing being less than about 60 decibels.

BRIEF DESCRIPTION OF THE DRAWINGS

The subject matter which is regarded as the invention is particularly pointed out and distinctly claimed in the concluding portion of the specification. The invention, however, may best be understood by reference to the following detailed description of various embodiments and accompanying drawings in which:

DETAILED DESCRIPTION OF THE INVENTION

As described in greater detail below, the various high-flow rate, low-noise, gas sampling apparatus in accordance with the present invention allow collection and detection of particulate or aerosol such as biological, chemical, and nuclear material and may be configured as a compact, unobtrusive, portable, lightweight apparatus for use in various indoor or outdoor locations. The ability of the apparatus to provide a high flow rate of gas to be sampled allows forming a concentrated sample particularly of small biological material such as anthrax or radioactive material such as from a dirty bomb compared to a low flow rate gas sampler.

The use of a fan results in a quiet, low power consumption apparatus compared to samplers employing a vacuum pump. The apparatus may be inconspicuously installed in businesses, workplaces, and residences. The apparatus may also include a sensor/collector for the detection/collection of radioactive material, a processor for monitoring operation of the apparatus, and the apparatus may be linked to a communications network such as the Internet.

Figures 1, 2:
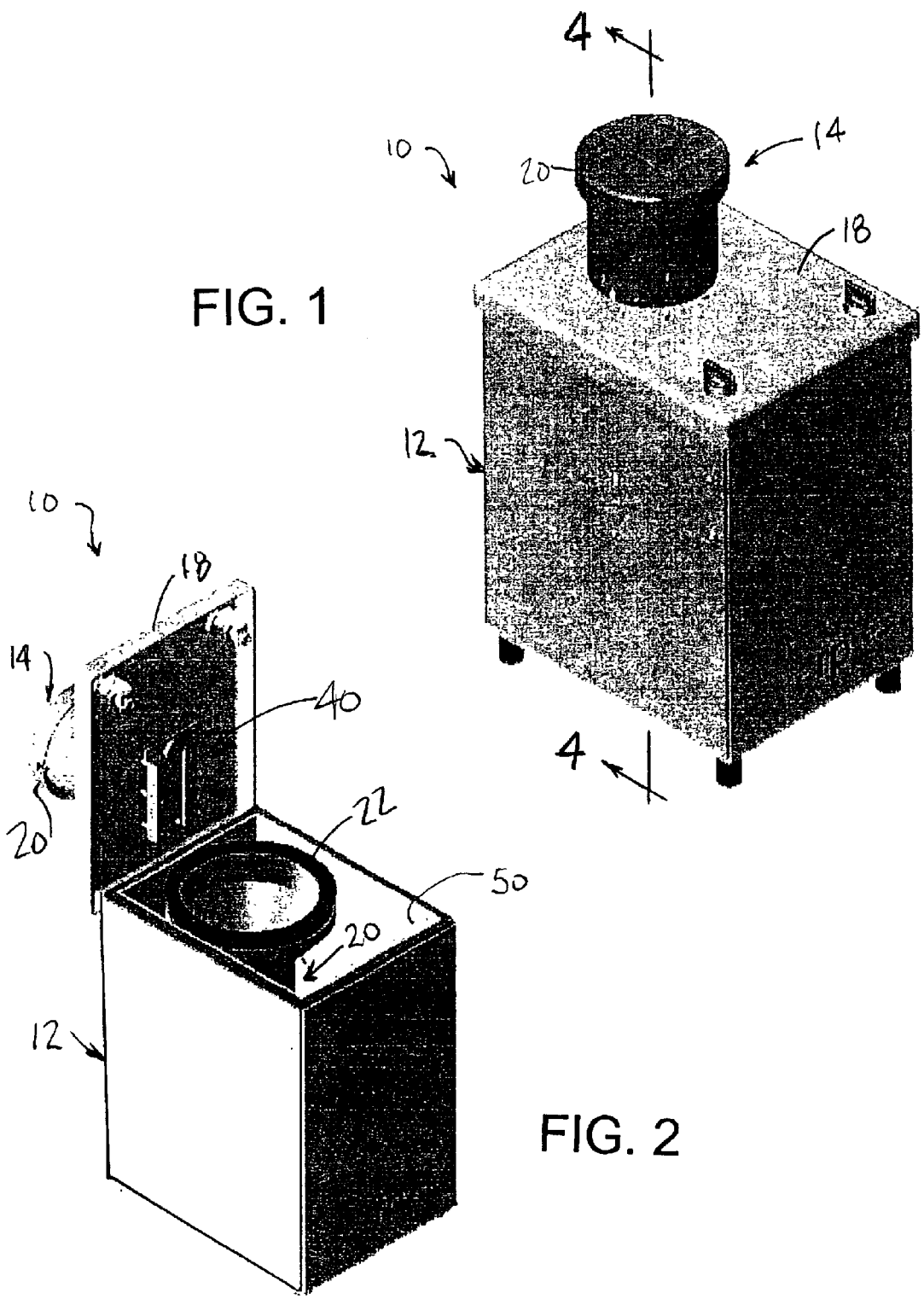
FIG. 1 is a front perspective view of a high-flow rate, low-noise, gas sampling apparatus in accordance with the present invention.
FIG. 2 is a front perspective view of the apparatus of FIG. 1 with the top opened.
Figure 3:
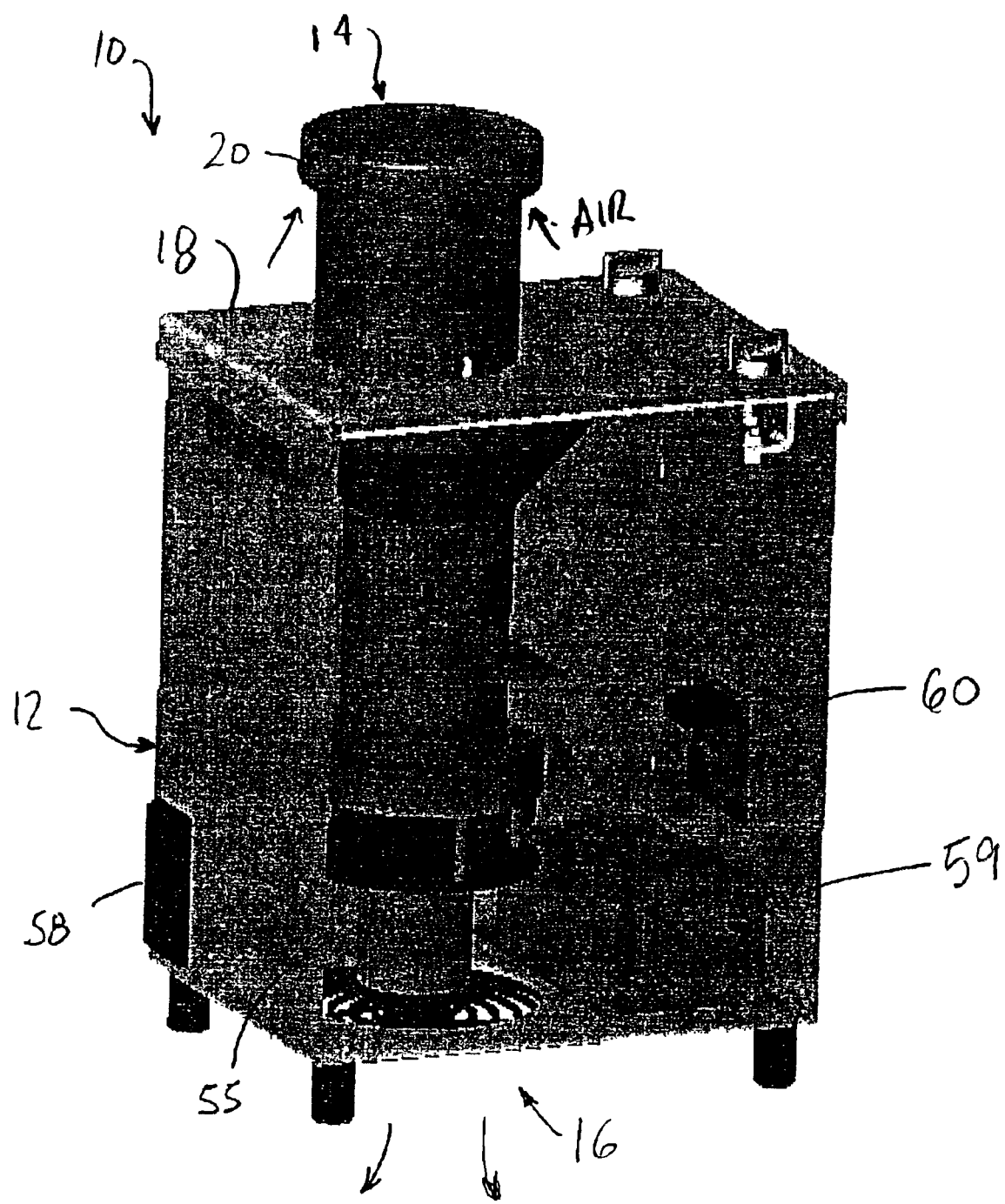
FIG. 3 is an enlarged rear perspective view of the apparatus of FIG. 1 with the rear portion of the housing removed.

FIGS. 1–3 illustrate a high-flow rate, low-noise, gas sampling apparatus 10 in accordance with the present invention for collecting particulate from a gas. As illustrated in FIGS. 1–3, apparatus 10 generally includes a housing 12 having an inlet 14 and an outlet 16 (FIG. 3). Disposed between inlet 14 and outlet 16 may be a hollow tubular-shaped member 20 (FIG. 3) having disposed therein a device such as a blower or a fan 30 (FIG. 3) for drawing the gas into the inlet, past a collector 40 (FIG. 2), through fan 30, and exhausting the gas through outlet 16. The apparatus may be compactly configured having, for example, a height of about 11 inches, a width of about 9 inches, and a depth of about 7 inches.

Fan 30 (FIG. 3) may be operable to produce a flow of gas through the housing of greater than about 50 liters per minute. A suitable sample of collected particulate may be obtained over an 8-hour time period. In addition, the fan may provide a flow of gas through the housing of about 100 liters per minute, 200 liters per minute, or greater thereby reducing the time to obtain a sample for analysis. Fan 30 may also generate little noise so that a noise level emitted from the housing is less than about 60 decibels. In addition, the noise level emitted from the housing may be less than about 55 decibels or lower. To reduce the level of noise from apparatus 10 further, sound reducing material or insulation 50 (FIG. 2) may be disposed on the inner surface of the housing. In addition, a muffler 55 (FIG. 3) may be disposed aft of the fan to further reduce the level of noise emitted from apparatus 10. A suitable high-flow rate, low noise fan is manufactured and available from Ameter-Rotron of Saugerties, N.Y., Model No. MF 501. The use of a fan, as noted above, also results in low power consumption and may be connected to an AC power supply (not shown) via an AC input connector 58 (FIG. 3), may be powered by a battery 59 (FIG. 3), and/or may include a backup battery power supply.

As best shown in FIG. 2, a top portion 18 of housing 12, may be hingedly-attached to allow an operator to readily install and retrieve a collector disposed in the housing. The upper portion of hollow tubular-shaped member 20 may also include a gasket 22 for sealing the upper portion of hollow tubular-shaped member 20 to the bottom of top portion 18 around collector 40.

Figure 4:
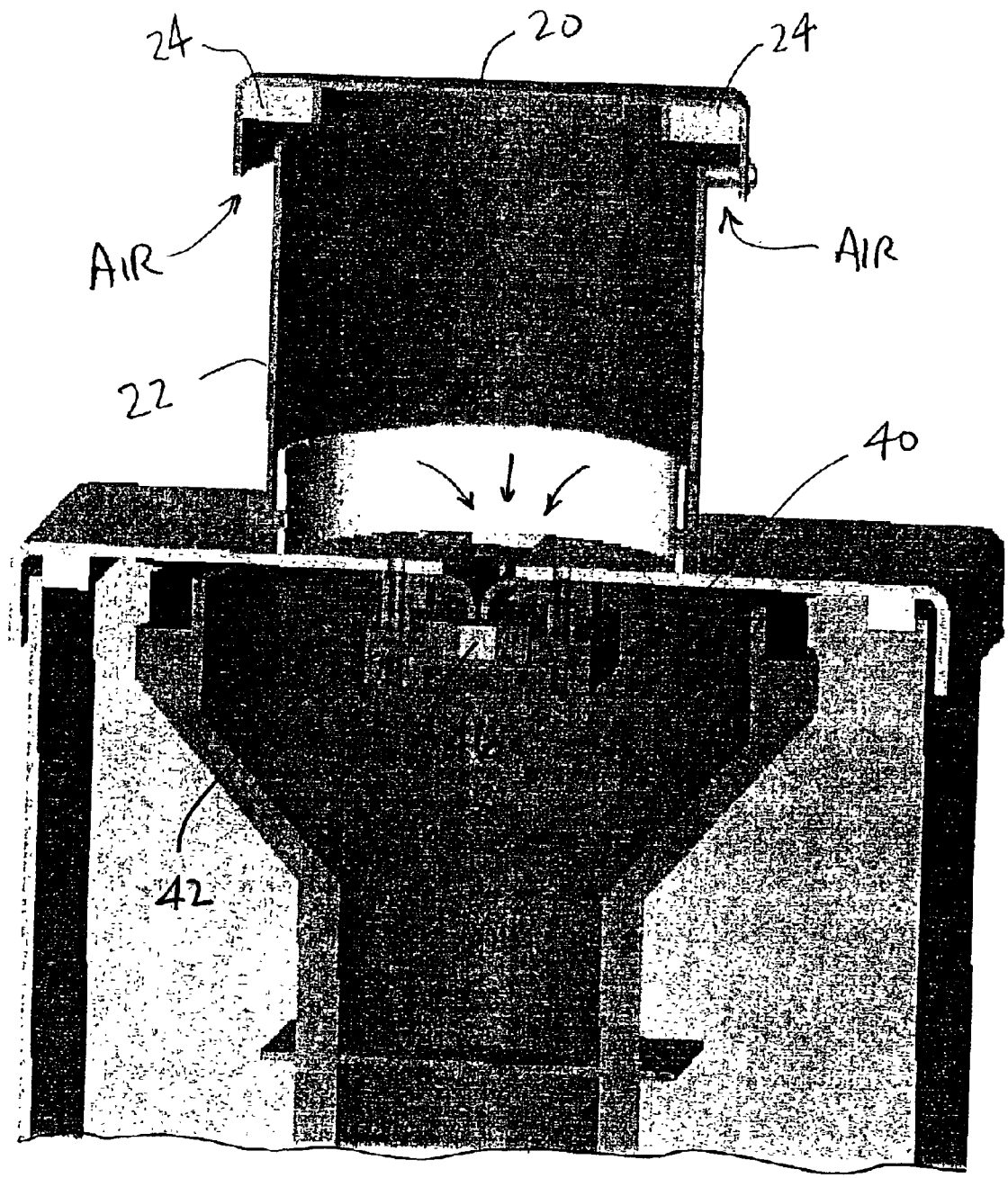
FIG. 4 is an enlarged partial sectional view of the apparatus of FIG. 1 taken along line 4—4.

With reference to FIG. 4, an impactor cap 21 may remove relatively large sized particles from the gas and directing the air towards collector 40 such as an impactor collector which may be disposed at the bottom of the top portion of the housing. Impactor cap 21 includes a cap 22 which attaches to top portion 18 of the housing and an impaction medium 24 through which the gas is initially in contact. Medium 24 may include geometry that removes particles with a diameter of 10 micrometers or more (0.0004 inches or one-seventh the width of a human hair). Impactor cap 21 (cap 22 and medium 24) may be replaceable or disposable, as well as the medium 24 being separately replaceable or disposable.

Figure 5:
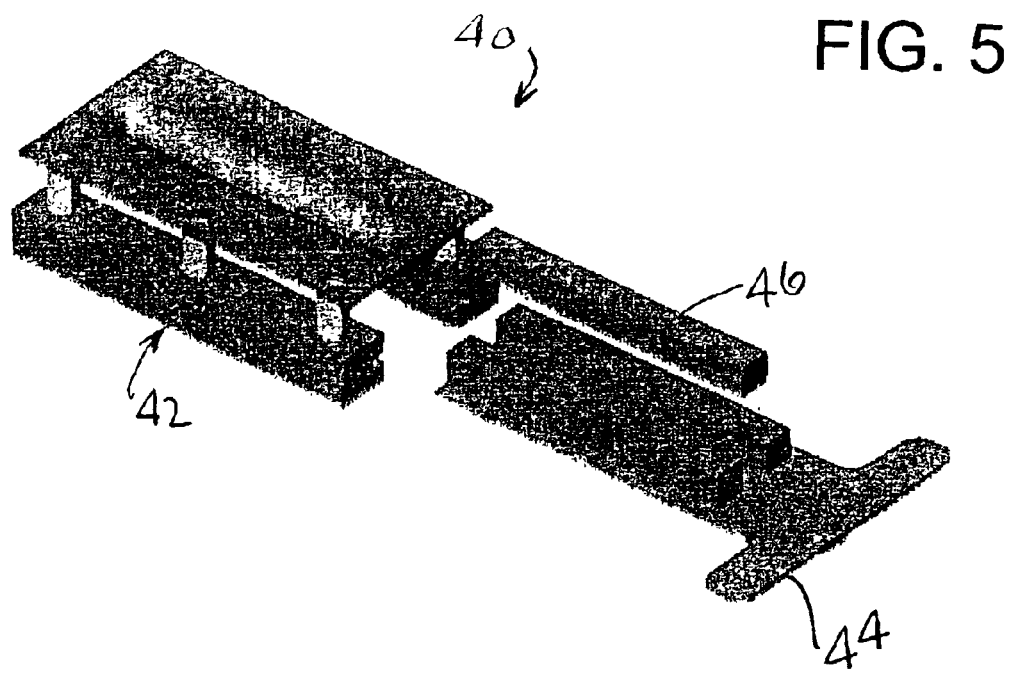
FIG. 5 is an enlarged perspective view of the holder and collector in accordance with the present invention for use in the apparatus of FIG. 1.
Figure 6:
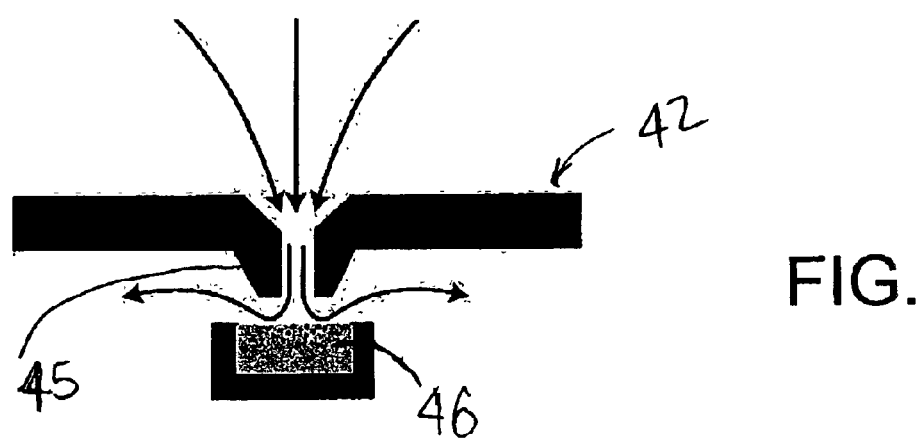
FIG. 6 is a sectional view of portions of the holder and collector of FIG. 5.

With reference to FIGS. 4 and 5, collector 40 may include a holder 42, a removable sample tray 44 which is receivable in holder 42, and a substrate 46 for collecting particulate which is receivable in sample tray 44. As best shown in FIG. 6, holder 42 includes a nozzle 45 shaped as a slit for channeling the air towards substrate 46. Substrate 46 may be comprised of polyurethane, polyethylene, polypropylene, polyester, porous cloth material, or other suitable material. The substrate may also be a porous material about 0.2 millimeters thick or greater. In one configuration, the substrate may comprise a polyurethane foam material having a density of about 0.005 g/cm3 to about 0.1 g/cm3. Particulate with a size of about 1.0 micron and larger may be collected on the substrate.

Advantages of the impact collector comprising a foam material include permitting a high flow rate of air to be sampled without clogging the collector or the slit in the holder, reducing particle bounce, eliminating the need to oil the substrate, inhibiting an increase in the pressure drop on the substrate as particles are accumulated on the substrate, concentrating the collection of particles in the upper portion of the substrate, and allowing the substrate to be formed from a generally inert material. While a slit impactor is shown, it will be appreciated that other shaped openings may be employed, e.g., square or round. Further impact collectors for use in the apparatus of the present invention are disclosed in U.S. patent application Ser. No. 09/540,397, entitled "Impaction Substrate and Methods of Use," issued as U.S. Pat. No. 6,435,043, the entire subject matter of which is incorporated herein by reference.

Figure 7:
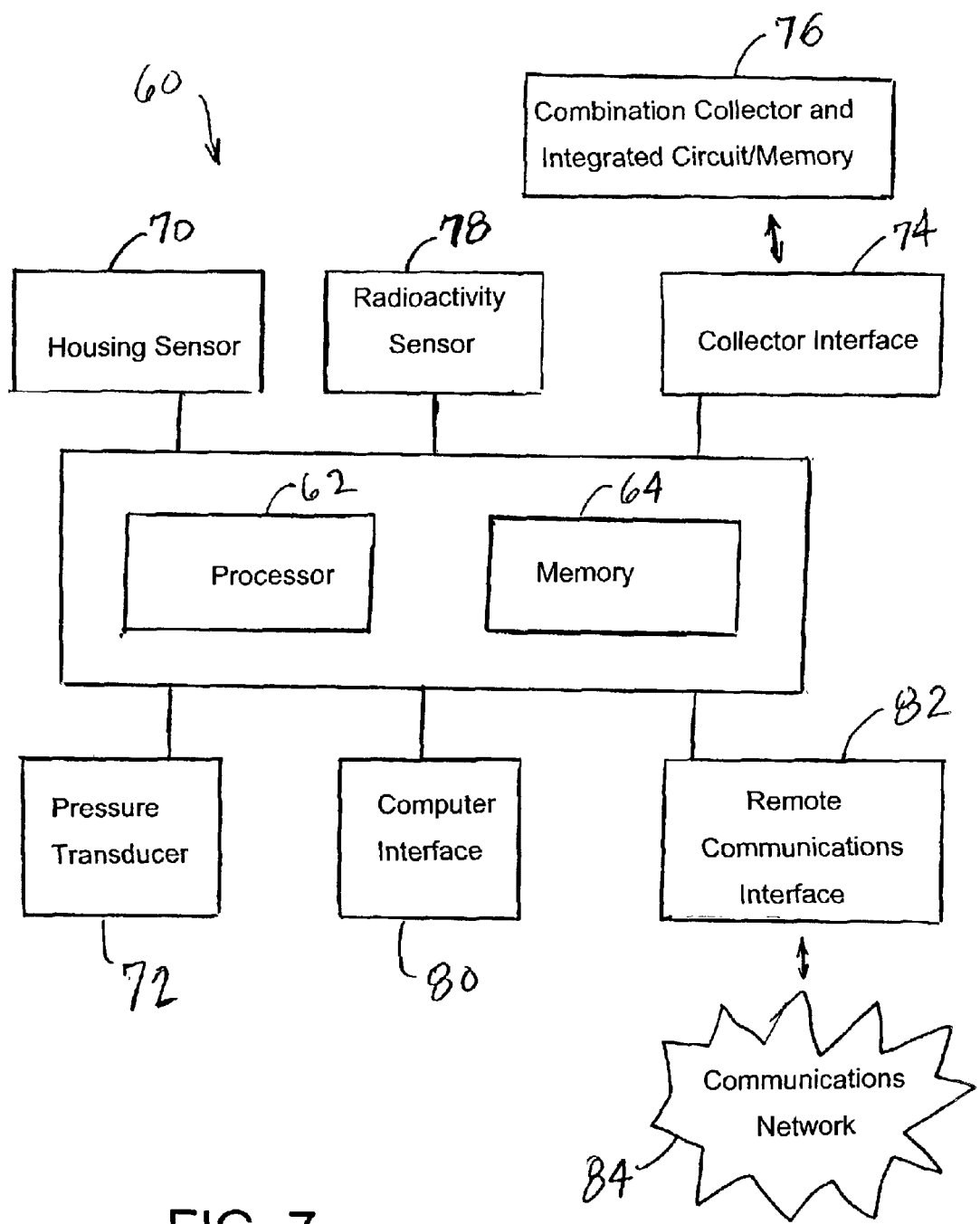
FIG. 7 is a diagrammatic illustration of the control unit of the apparatus of FIG. 1.

With reference again to FIG. 3, apparatus 10 may include a control unit 60 for monitoring the operation of apparatus 10. As best shown in FIG. 7, control unit 60 may include a processor 62 such as a microcontroller or a microprocessor, data storage or memory 64, and various input and output devices. A suitable processor is manufactured by and available from Texas Instruments of Dallas, Tex., Model No. MSP430. The data storage or memory may be either physically integrated with the processor or constructed in stand alone units.

As illustrated in FIG. 7, the various input devices may include a housing sensor 70 such as an electrical switch for detecting the opening and/or closing of the top portion of the housing and a differential pressure sensor or pressure transducer 72 for measuring the pressure drop across the collector. Housing sensor 70 and pressure transducer 72 may be used for setting the time and date of the beginning of a sampling process, setting the time and date of the ending of the sampling process, and/or setting the time and date of an opening of the top portion of the apparatus or detection of a change in flow of gas through the apparatus during the sampling process, e.g., which may indicate a malfunction of or tampering with the apparatus such as blocking of the inlet during the running of a sampling process. In addition, opening the top portion of the housing may automatically stop the sampling process, e.g., stop the blower and recording the stop time of the sampling process.

Other input devices may include a collector interface 74 for connecting and transferring data to and from a combination collector and integrated circuit/memory 76. Data transferred from the processor and to the combination collector and integrated circuit/memory may include the start time and date of the sampling process, the ending time and date of the sampling process, location of the sampler, etc. The uploading to the integrated circuit/memory may occur automatically upon opening of the top portion of the housing. Combinations of collector and integrated circuit/memory are described in U.S. Pat. No. 5,717,147, the entire subject matter of which is incorporated herein by reference, and the features thereof may be incorporated into the collectors of the present invention.

Another sensor may include a Geiger counter or radioactivity sensor 78 for detecting and signaling, in realtime, the presence of radioactive material passing through the apparatus or presence of radioactive material in collection of particulate on the substrate. The radioactivity sensor may be, for example, disposed within tubular-shaped member 20 (FIG. 3), disposed adjacent to substrate 46 (FIG. 4), attached to the bottom of the top portion of the housing or attached to holder 42. A suitable radioactivity sensor is manufactured and available from LND, Inc. of Oceanside, N.Y., Model No. 713. Alternatively, each replaceable holder and substrate may include a radioactivity sensor operably connectable to control unit 60. Still another sensor may include a power supply sensor for detecting a loss of electrical power to the apparatus. Yet another sensor may include a particle counter for counting the number of particles/volume of gas such as Model GT-531 manufactured and available from Met-One Instruments, Inc., Grants Pass, Oreg.

Control unit 60 may also include a computer interface 80 such as an RS-232 connector or infrared port to allow an operator to connect the apparatus to a laptop computer or other handheld device for transfer of data therebetween such as site information, time, date, and other parameters.

Control unit 60 may also include a remote communications interface 82 such as a modem or wireless transmitter for remotely uploading or downloading data, periodically or in realtime, over a communications network 84 such as a local area network, global communications network, or the Internet.

Figures 8, 9:
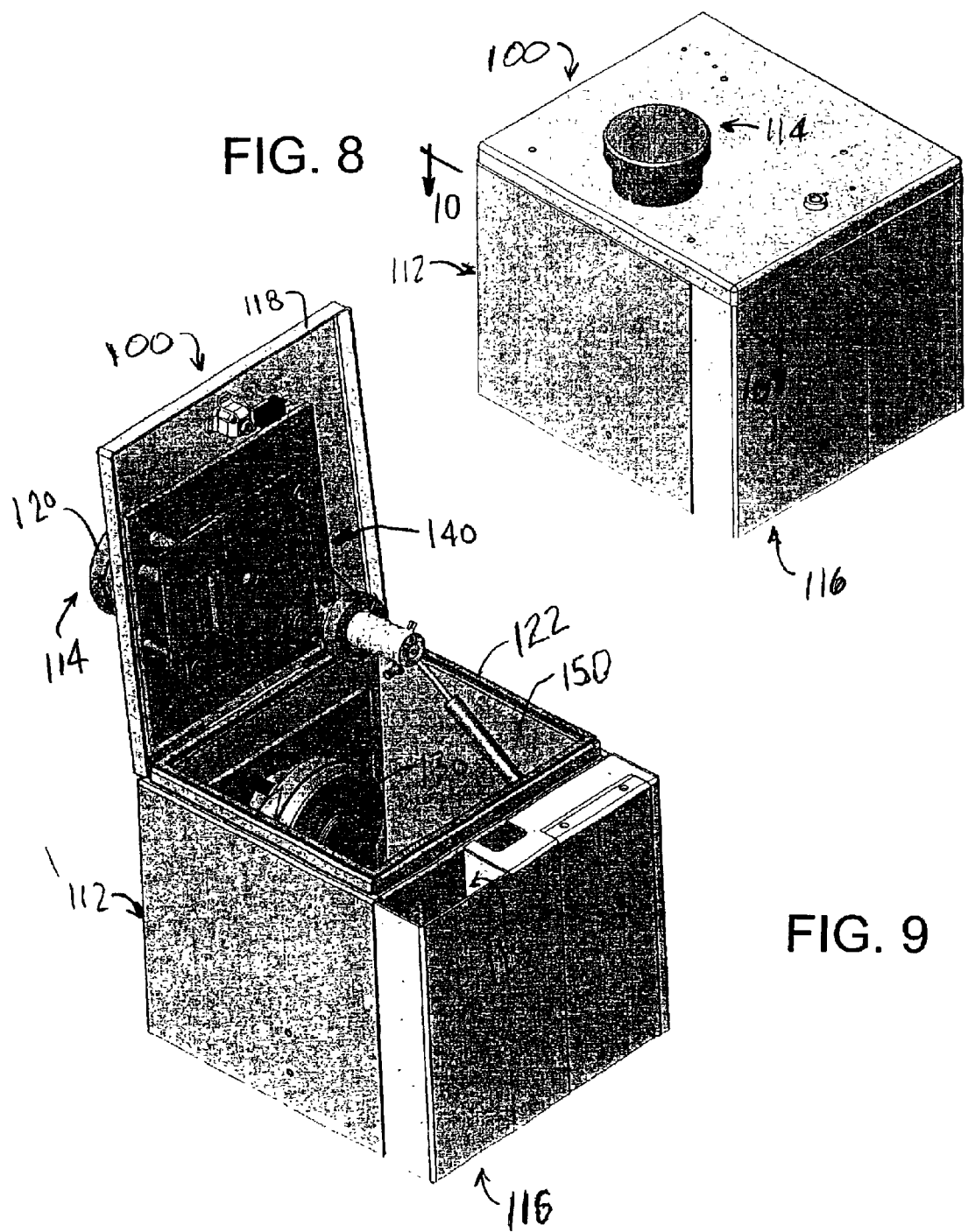
FIG. 8 is a front perspective view of another high-flow rate, low-noise, gas sampling apparatus in accordance with the present invention.
FIG. 9 is a front perspective view of the apparatus of FIG. 8 with the top opened.
Figure 10:
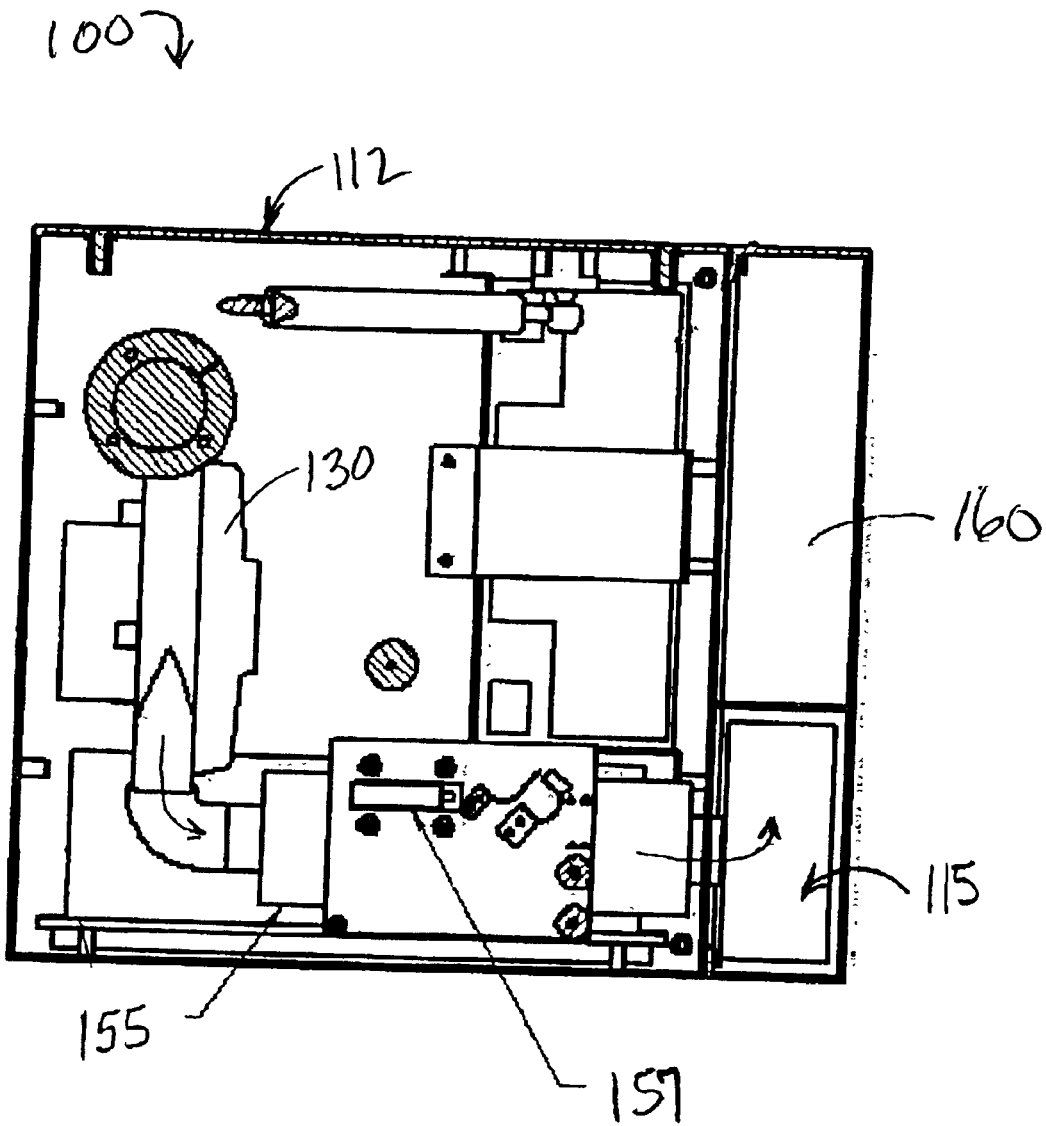
FIG. 10 is an enlarged sectional view of the apparatus of FIG. 8 taken along line 10—10.

FIGS. 8 and 9 illustrate another high-flow rate, low-noise, gas sampling apparatus 100 in accordance with the present invention for collecting particulate from a gas. In this illustrated apparatus, apparatus 100 generally includes a housing 112 having an inlet 114, and an outlet 116 disposed on the bottom of the housing. With reference to FIGS. 9 and 10, a device such as a blower or a fan 130 creates a vacuum in housing 112 for drawing the gas through inlet 114 (FIG. 9), past one of a plurality of collectors 140 (FIG. 9), through fan 130, through a muffler 155 (FIG. 10), past a Geiger counter or radioactivity sensor 157 (FIG. 10), and out the bottom of the housing via a chamber 115 disposed along the side of housing 112.

Fan 130 may be operable to produce a flow of gas through the housing of greater than about 50 liters per minute. In addition, the fan may provide a flow of gas through the housing of about 100 liters per minute, 200 liters per minute, or greater, and generate little noise so that a noise level emitted from the housing is less than about 60 decibels and desirably less than about 55 decibels. To further reduce the level of noise from apparatus 100, sound reducing material or insulation 150 (FIG. 9) may be disposed on the inner surfaces of the housing in addition to muffler 155. A suitable high-efficiency fan for use in apparatus 100 is described above in connection with apparatus 10.

A top portion 118 of housing 112, best shown in FIG. 9, may be hingedly-attached to readily allow an operator access to a carousel or revolving case for installing and retrieving a plurality of collectors disposed in the housing. The upper portion of the sides of housing 112 may include a gasket 122 for sealing the upper side portions of housing 112 to the bottom of top portion 118. An impactor 120 may provide filtering of relatively large sized particles from the gas being sampled as described above in connection with apparatus 10.

Figure 11:
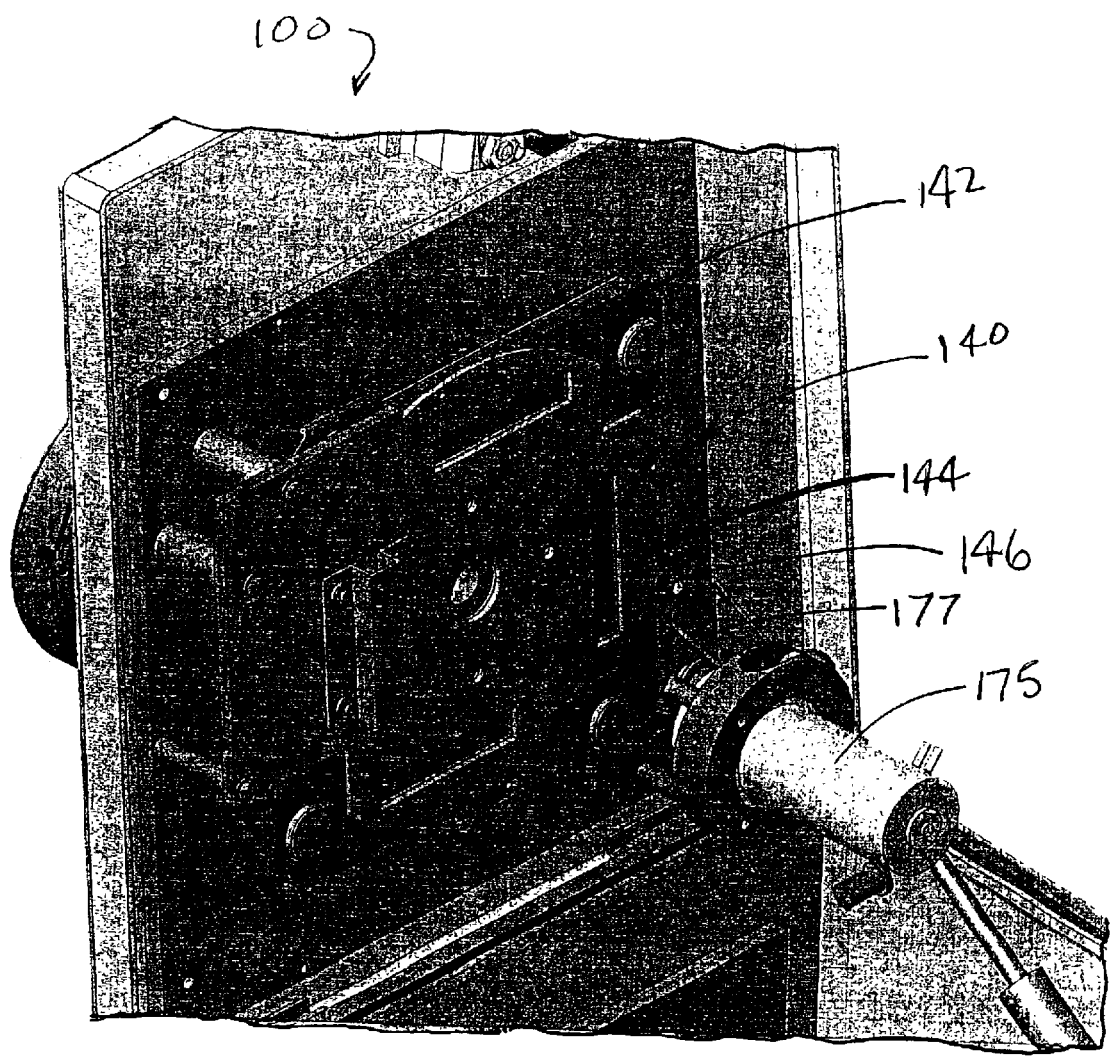
FIG. 11 is an enlarged perspective view of the carousel for holding a plurality of collectors of FIG. 1.
Figure 1:
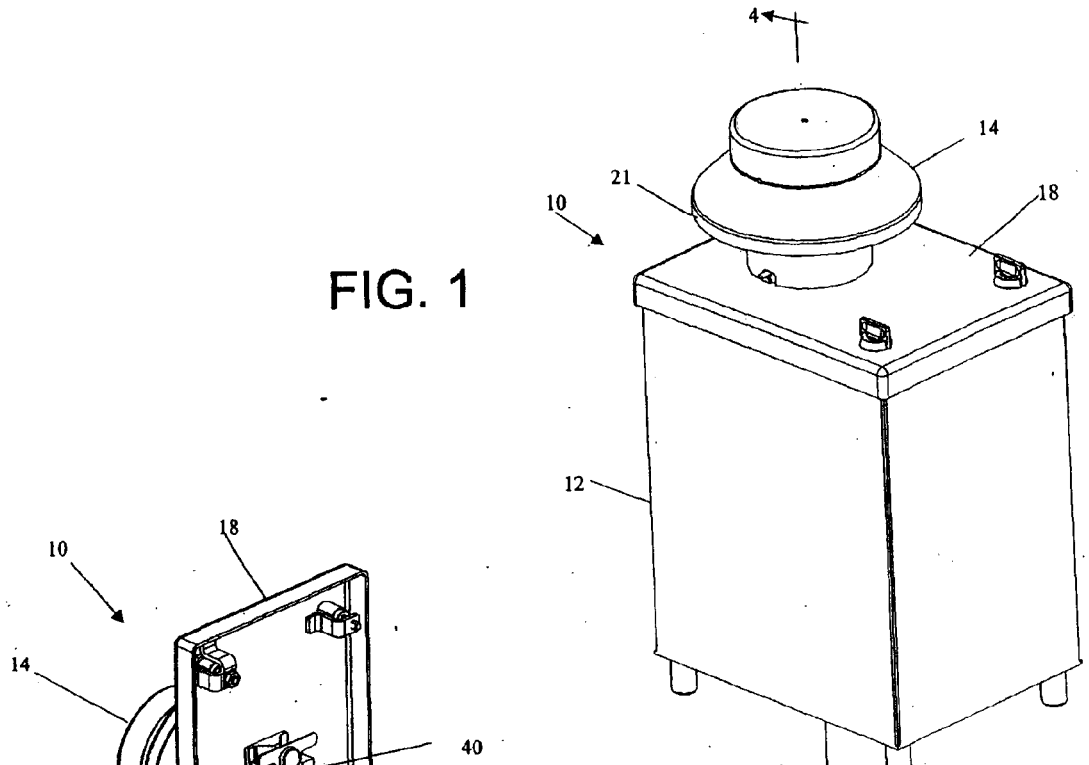
Figure 2:
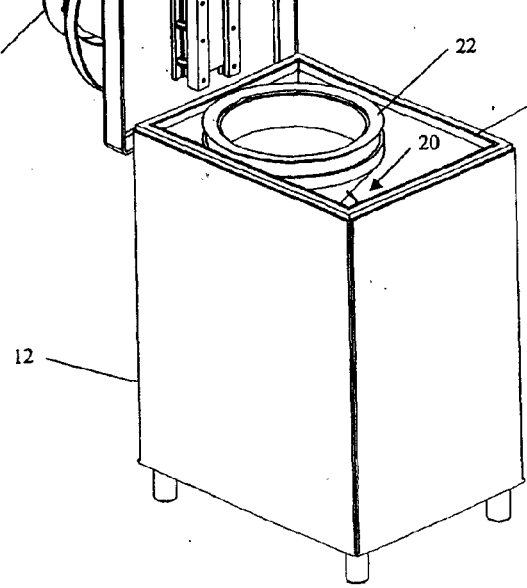
Figure 3:
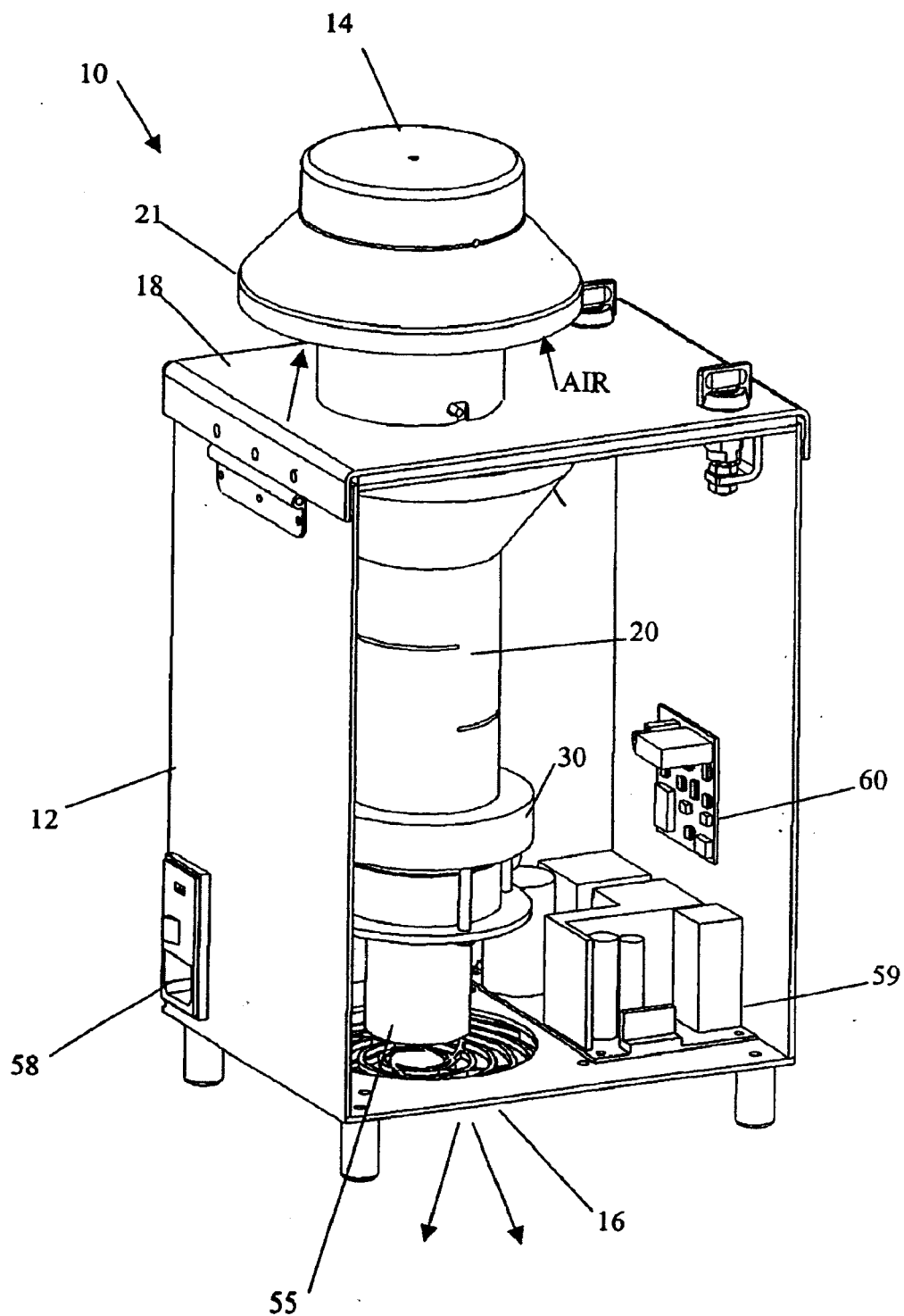
Figure 4:
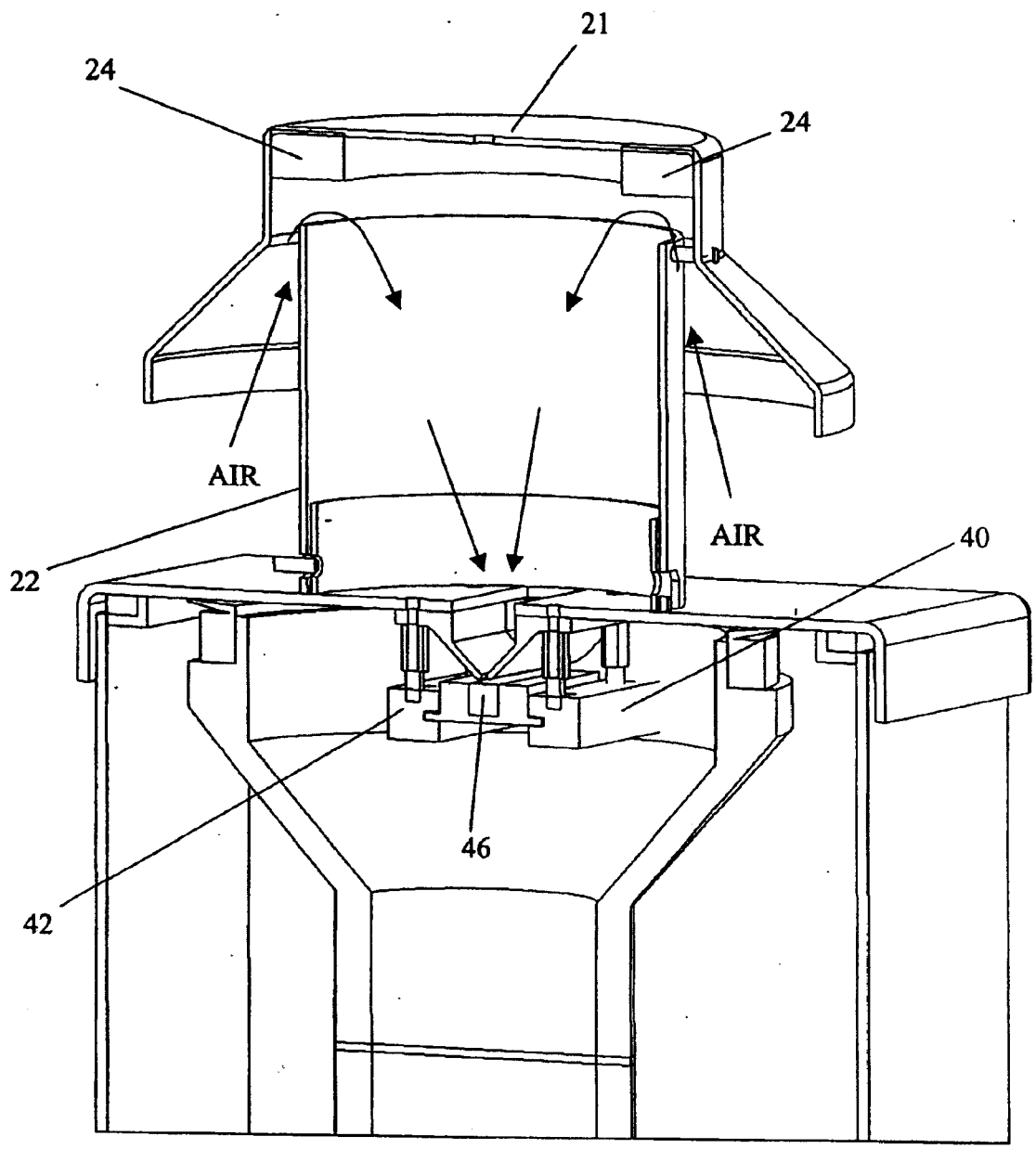
Figure 5:
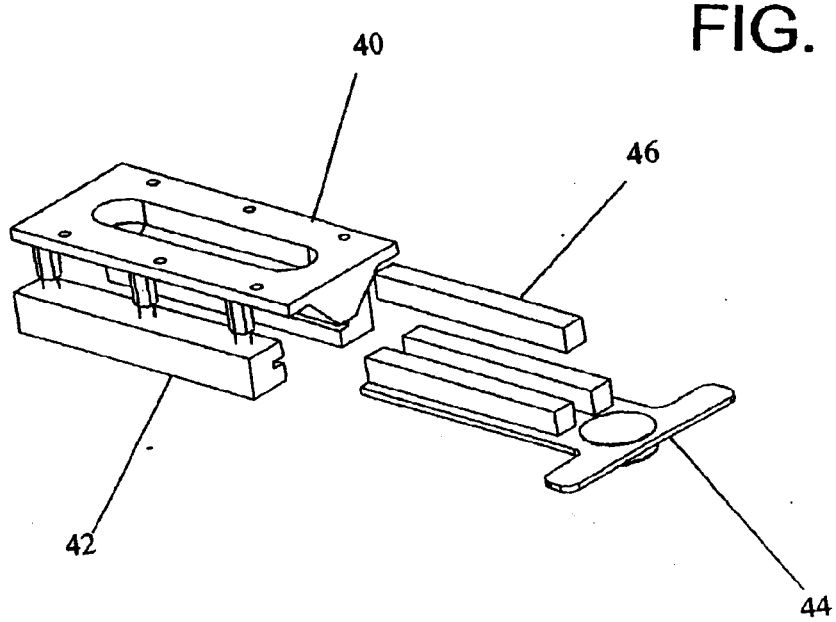
Figure 6:
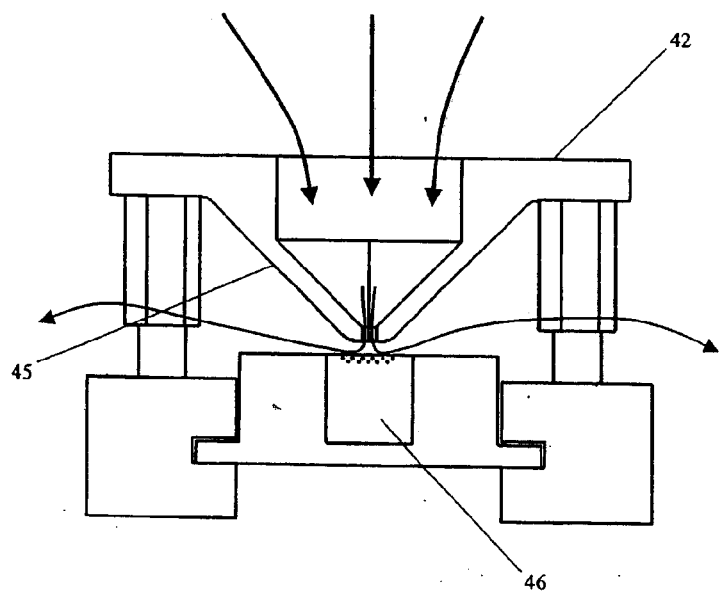
Figure 7:
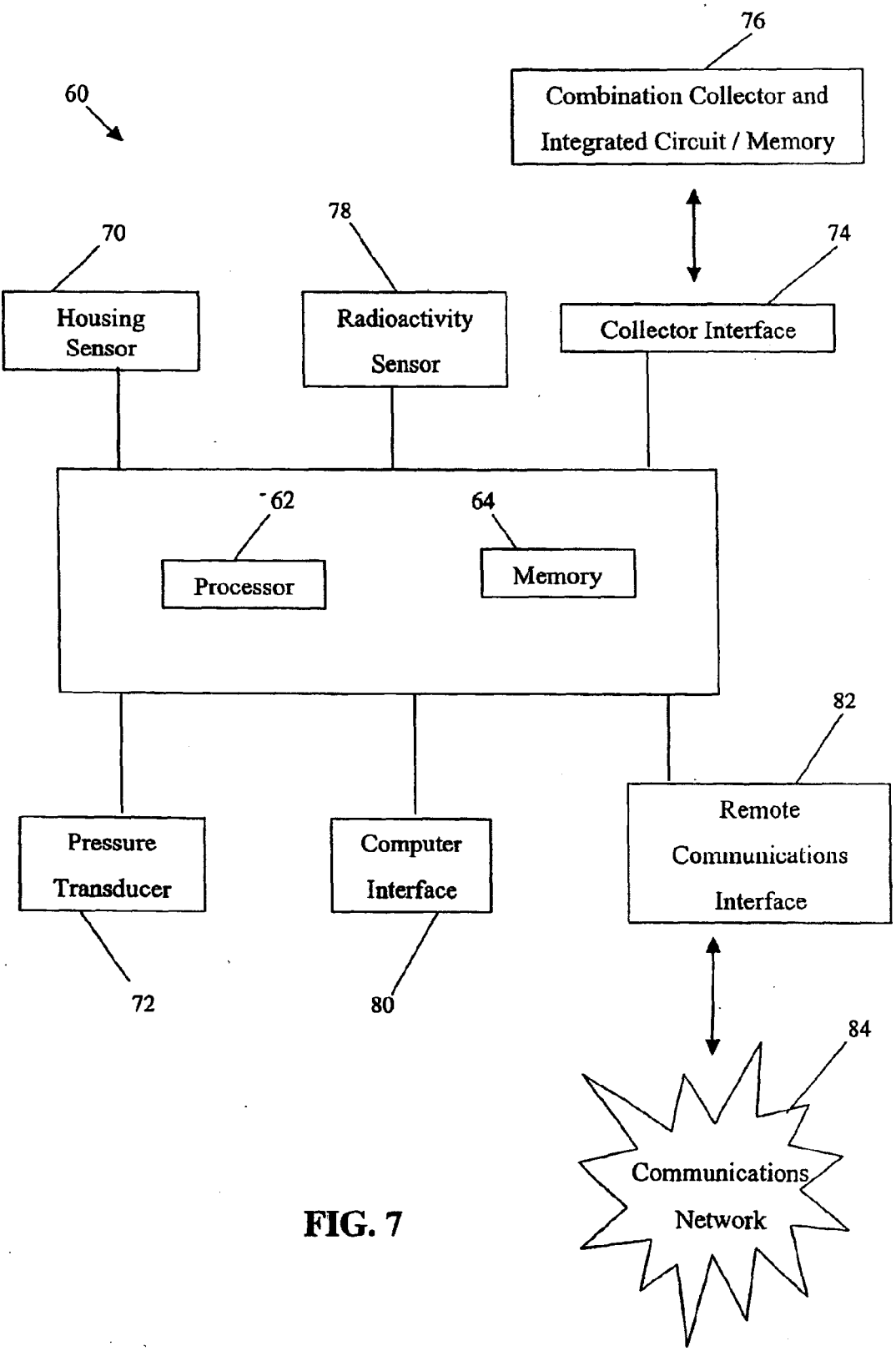
Figure 8:
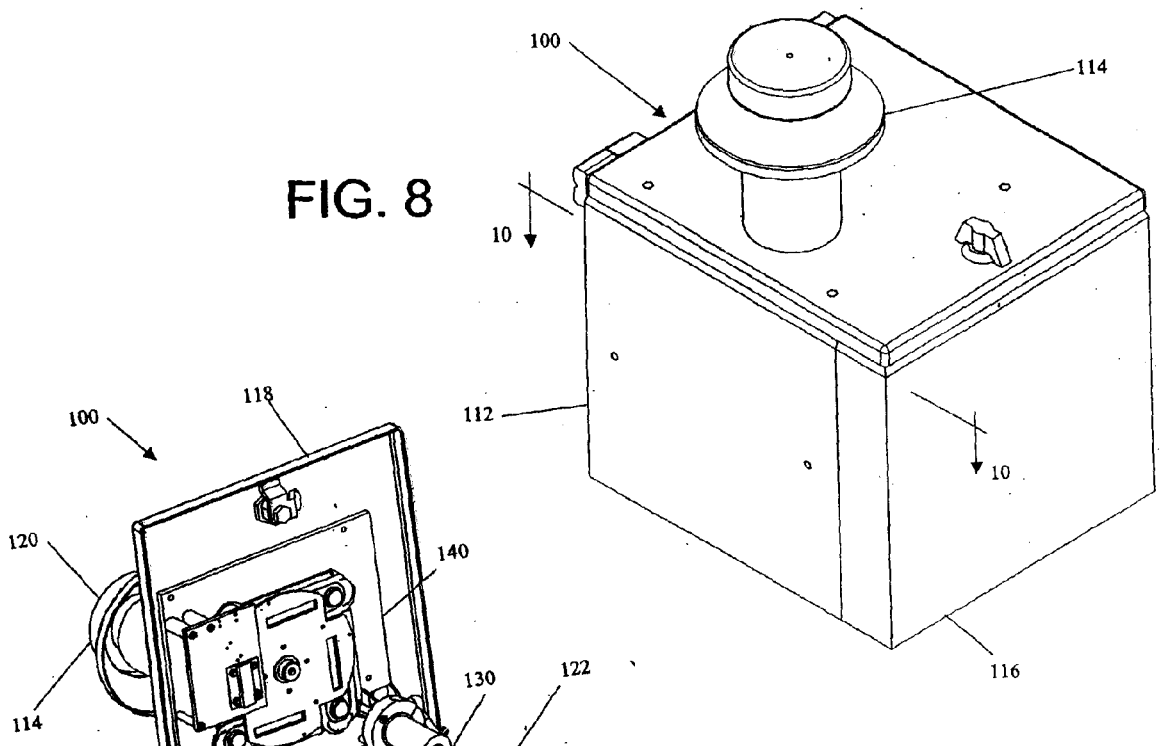
Figure 9:
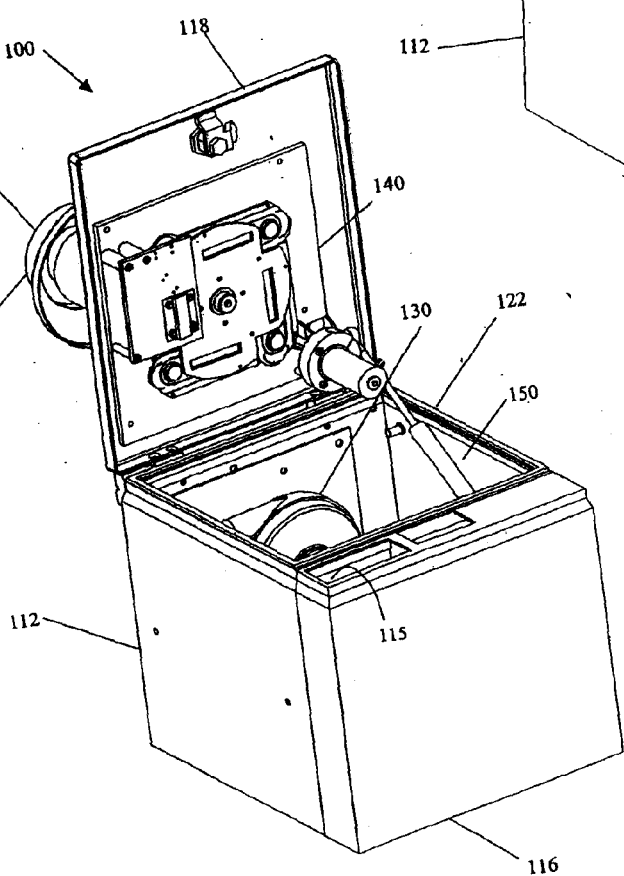
Figure 10:
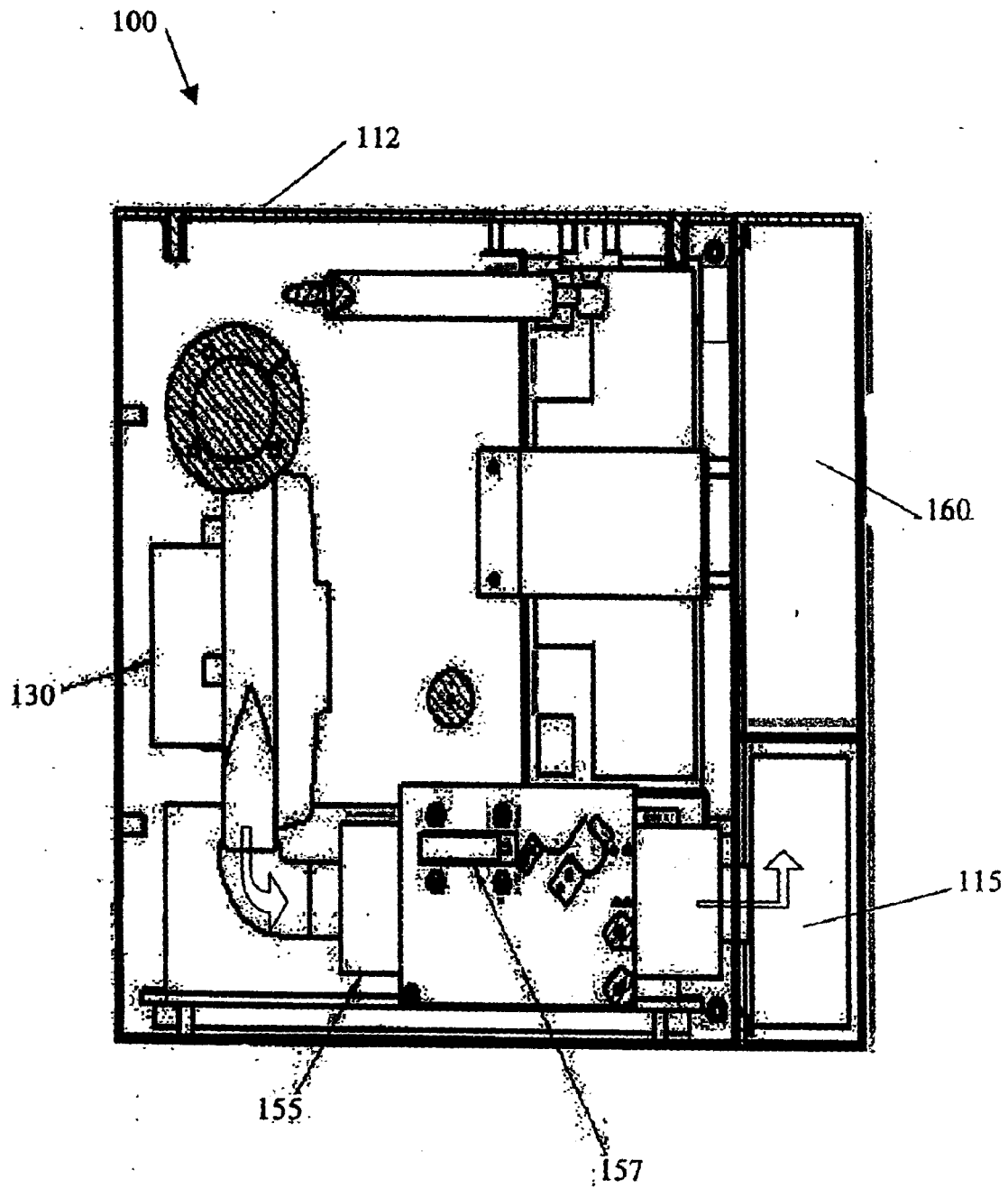
Figure 11:
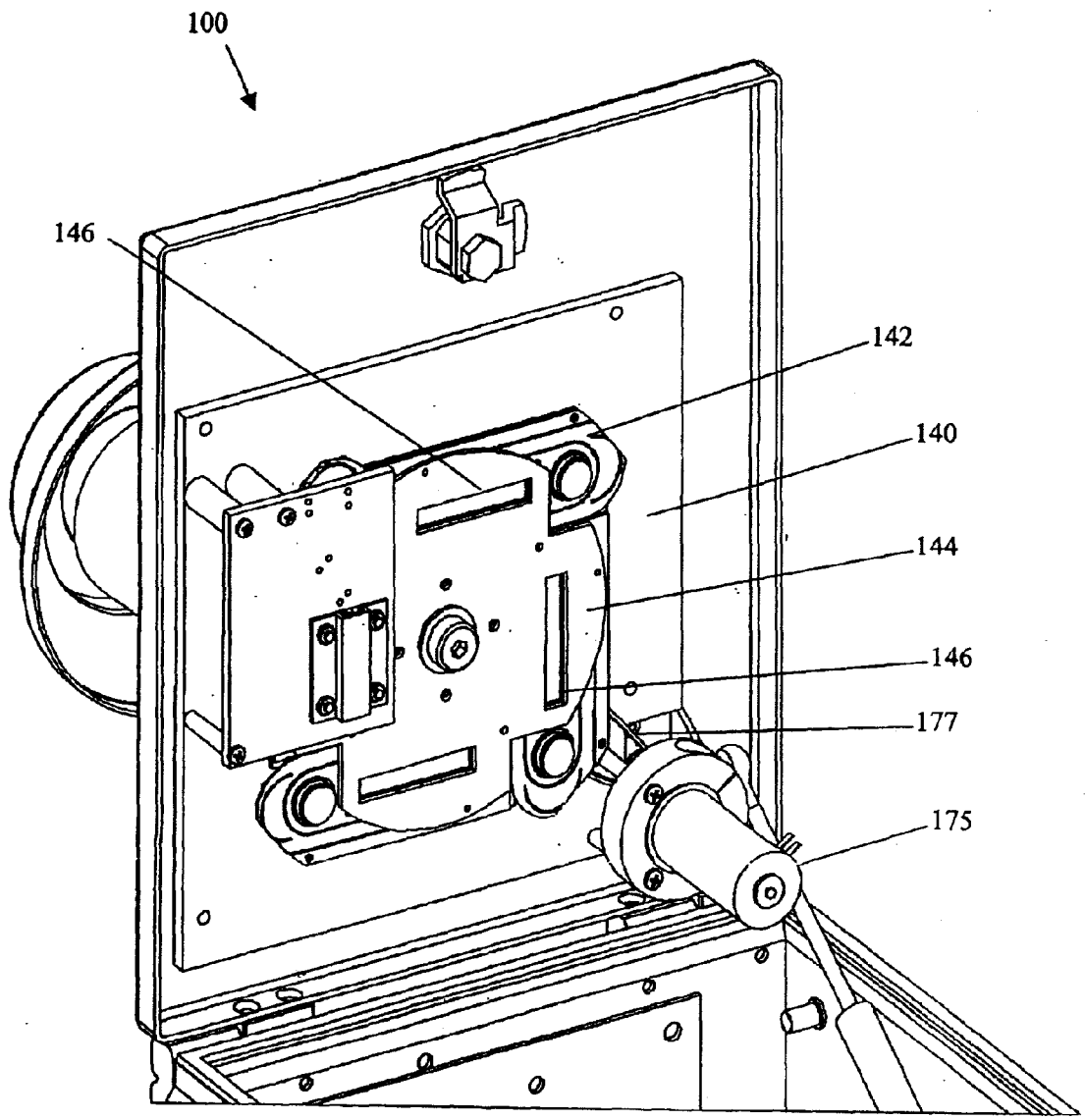
Figure 1:
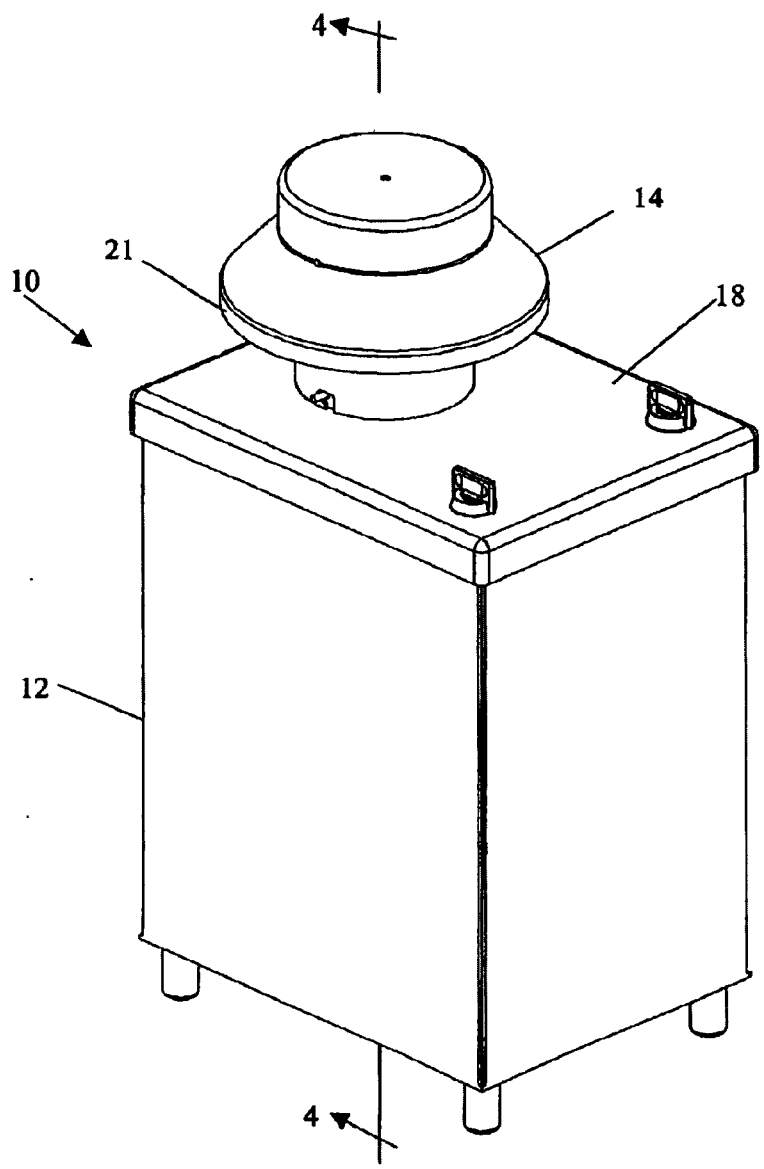
Figure 2:
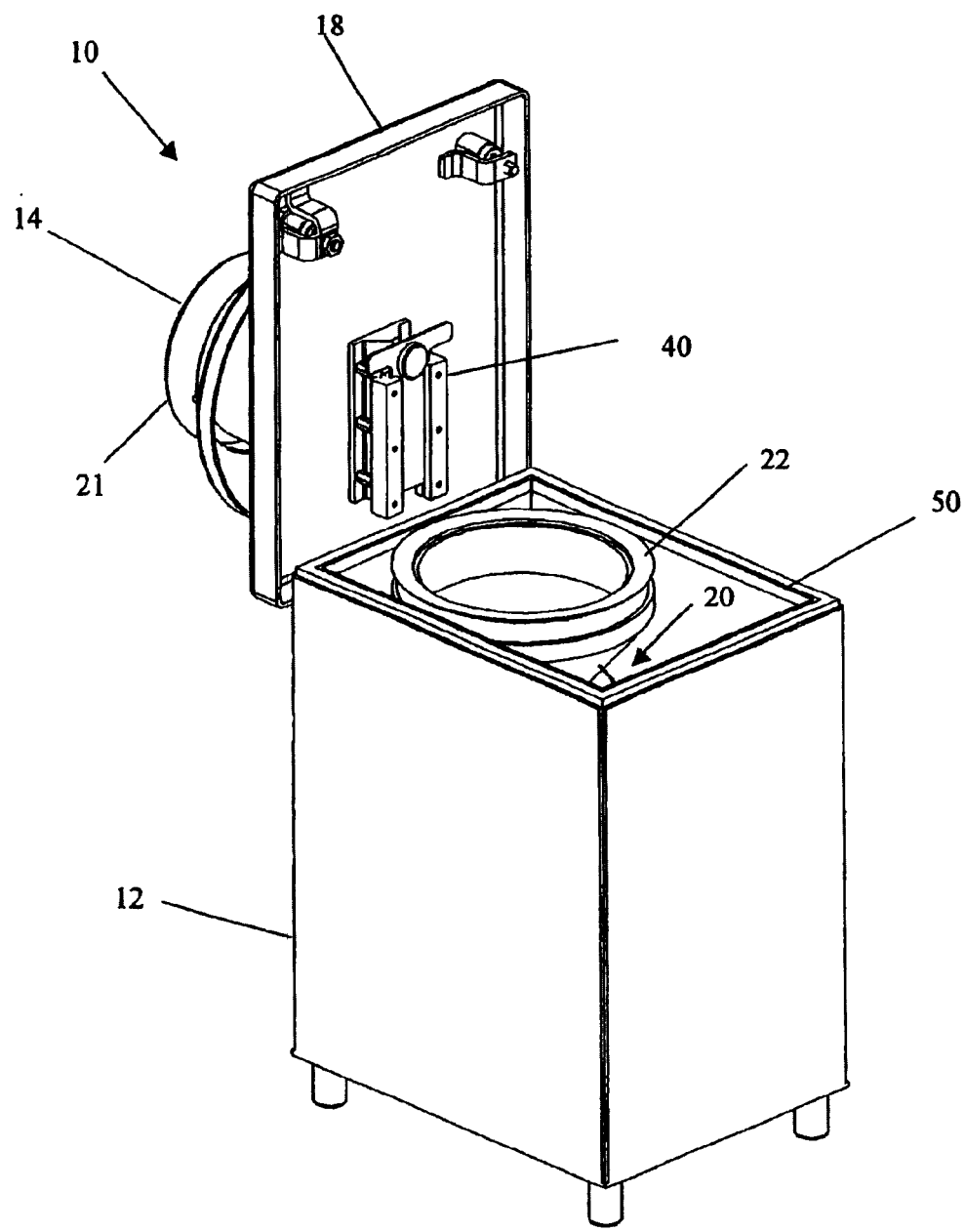
Figure 3:
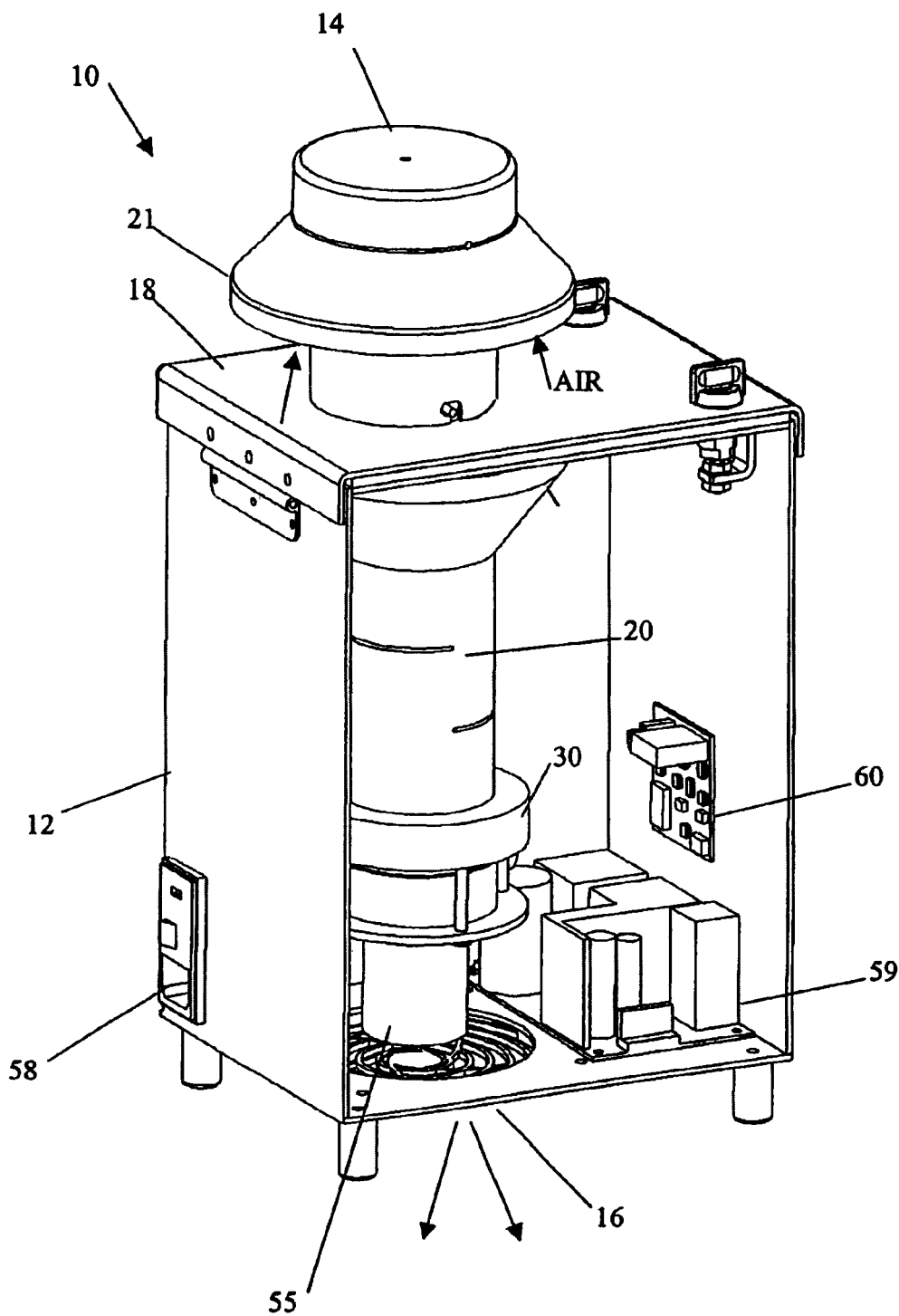
Figure 4:
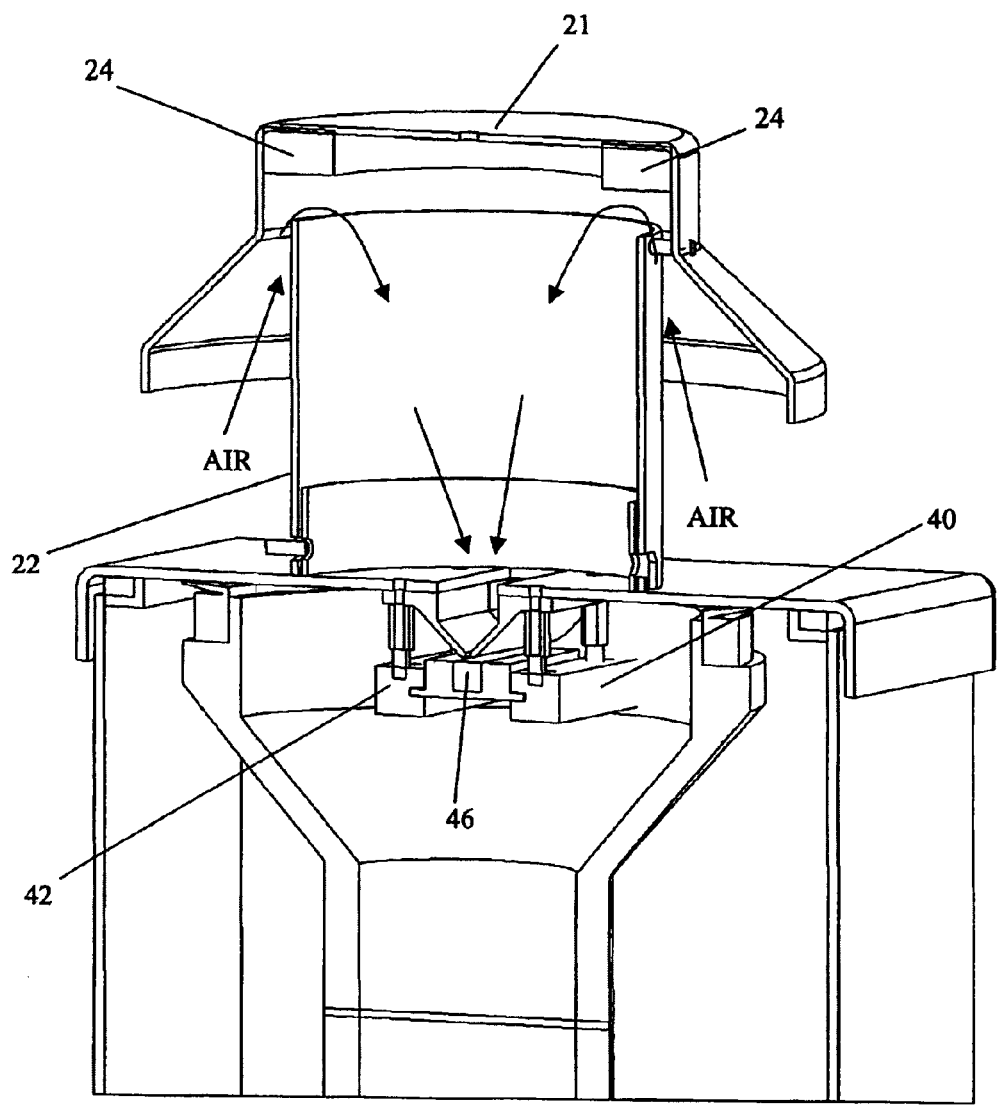
Figure 5:
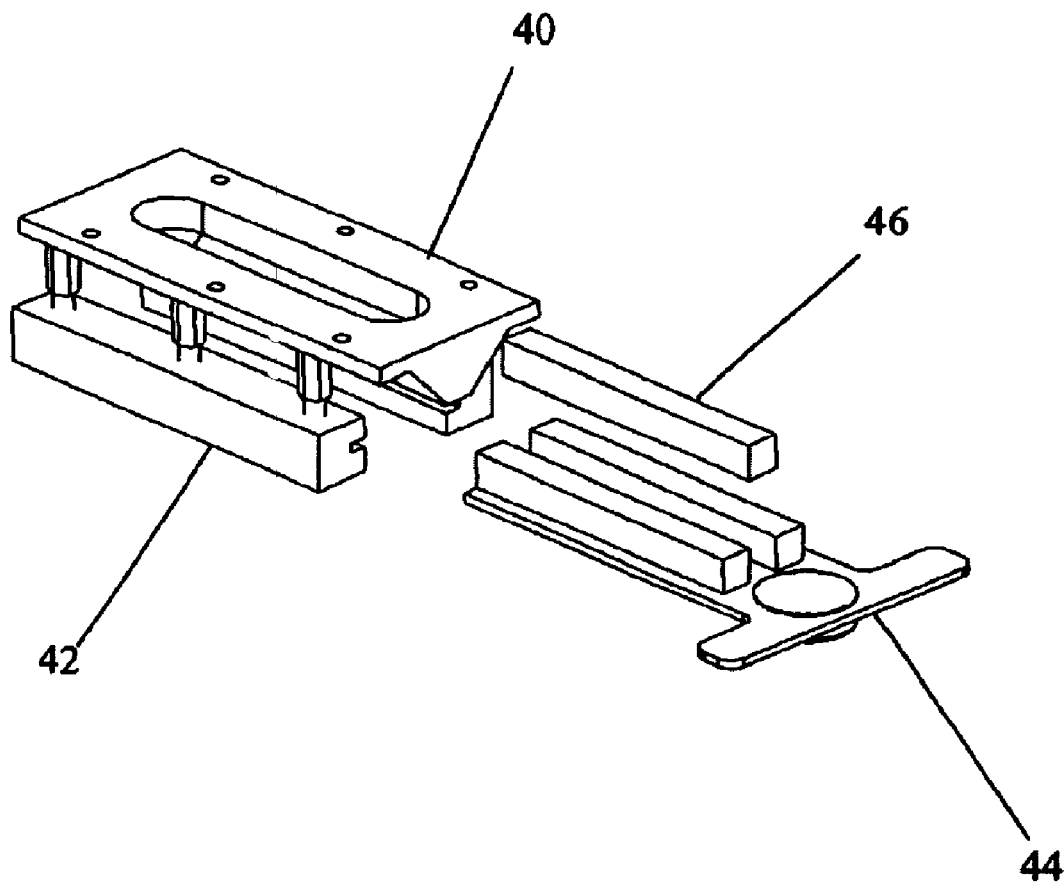
Figure 6:
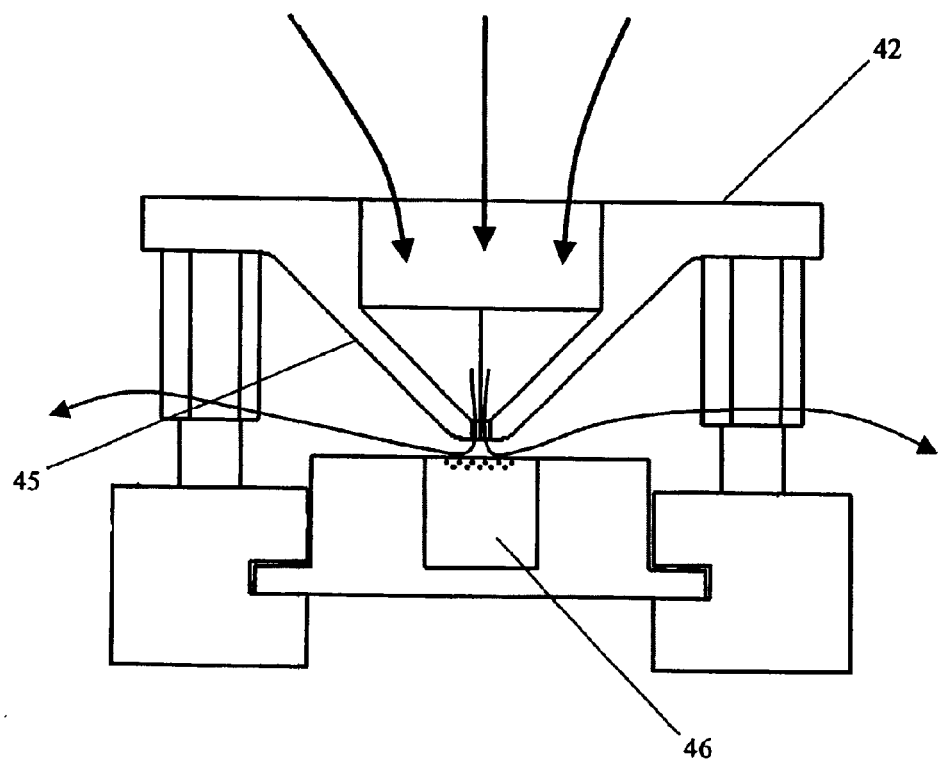
Figure 7:
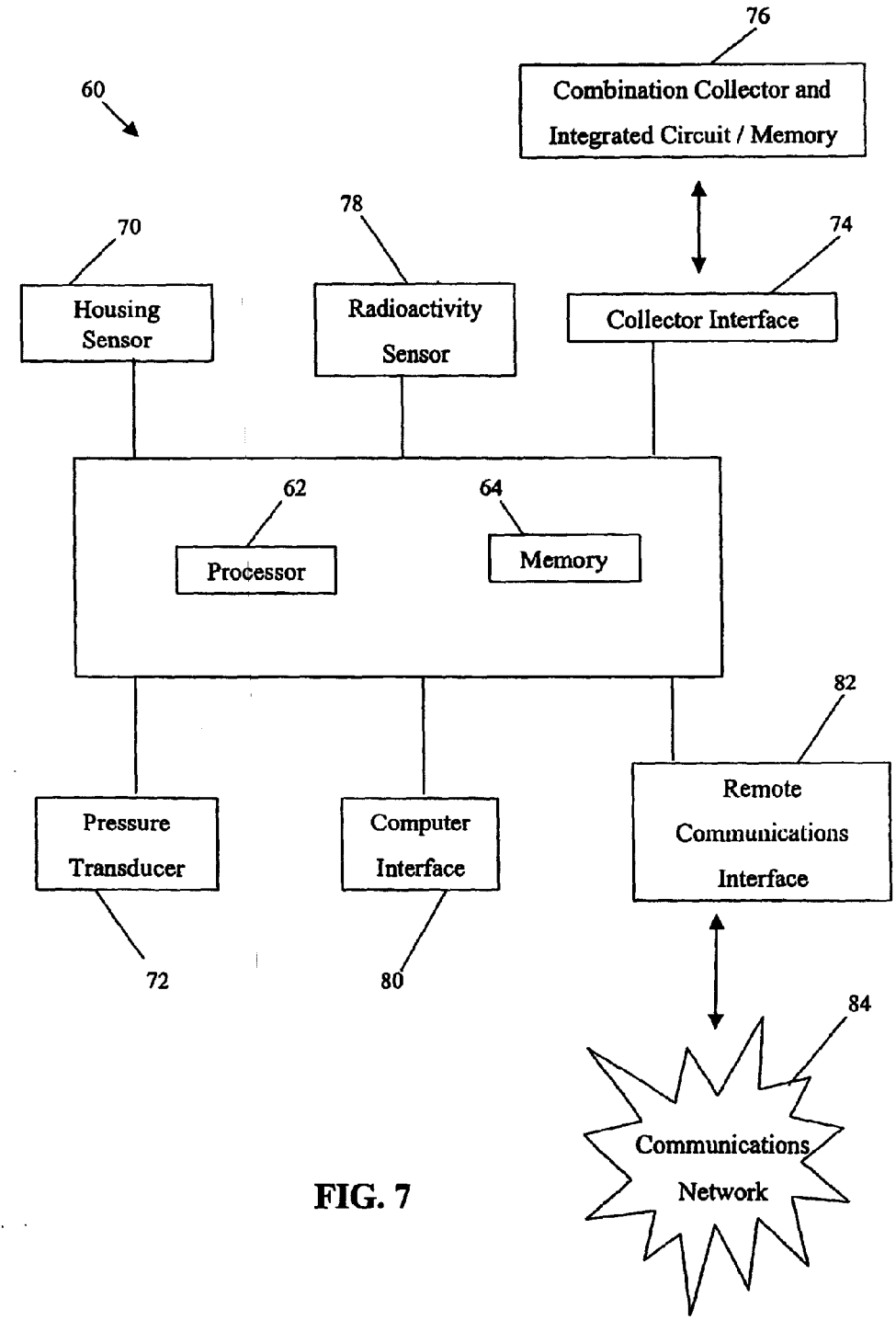
Figure 8:
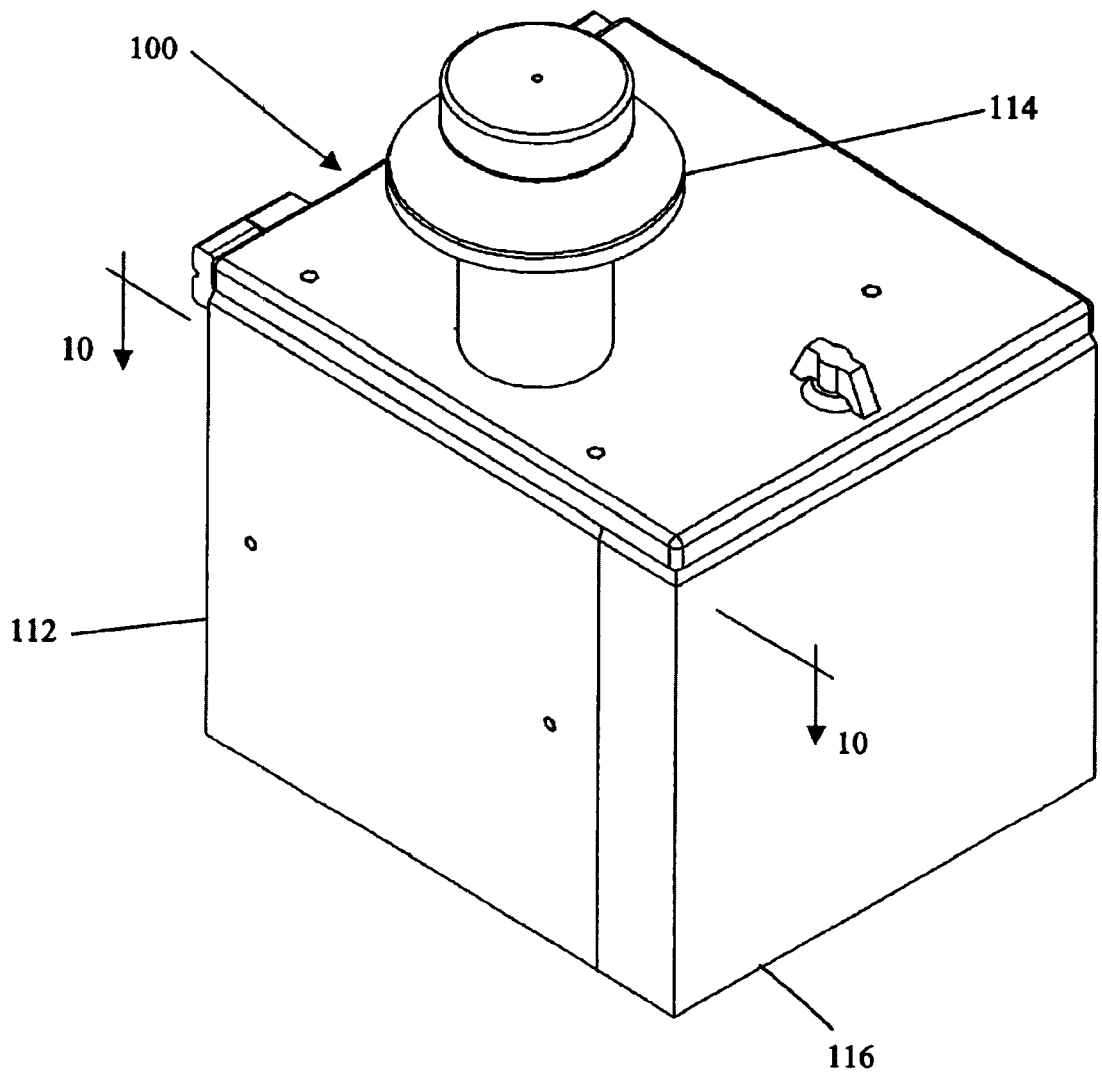
Figure 9:
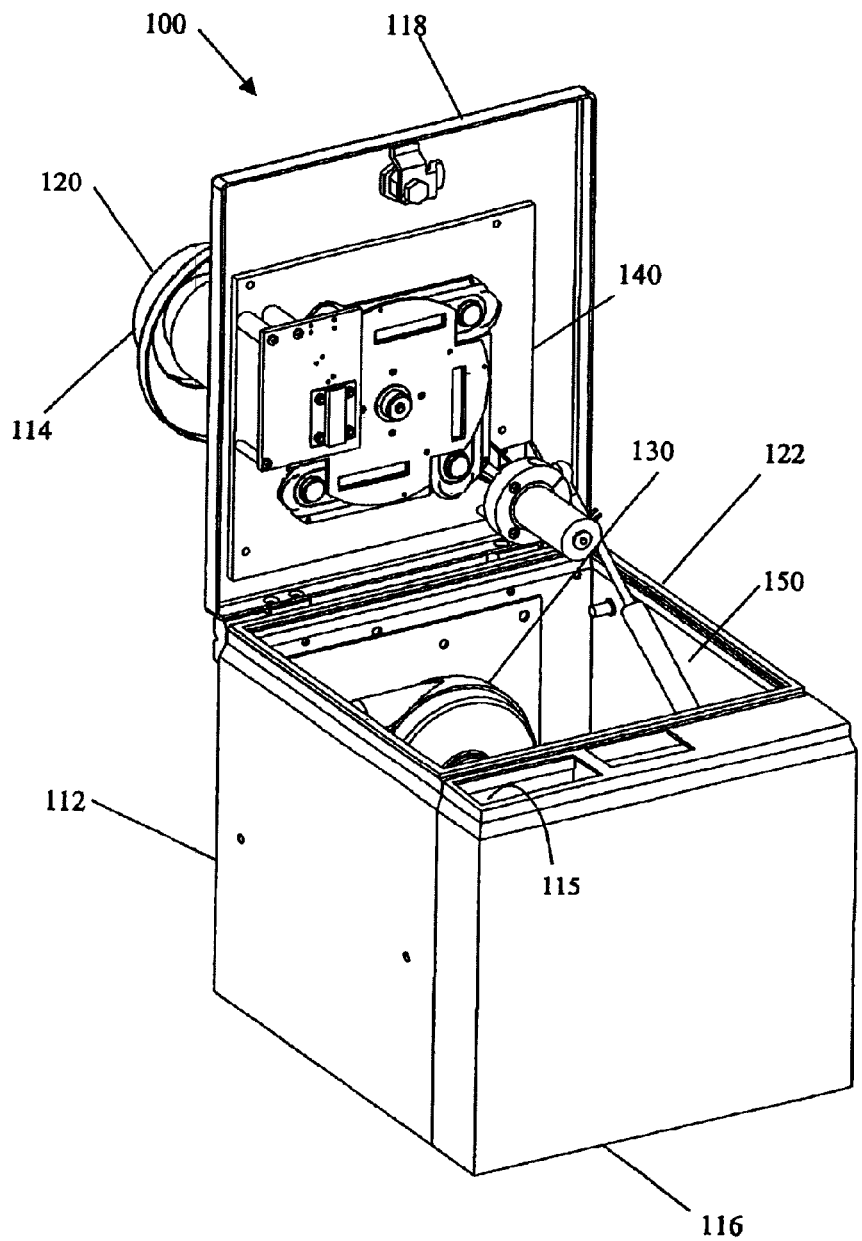
Figure 10:
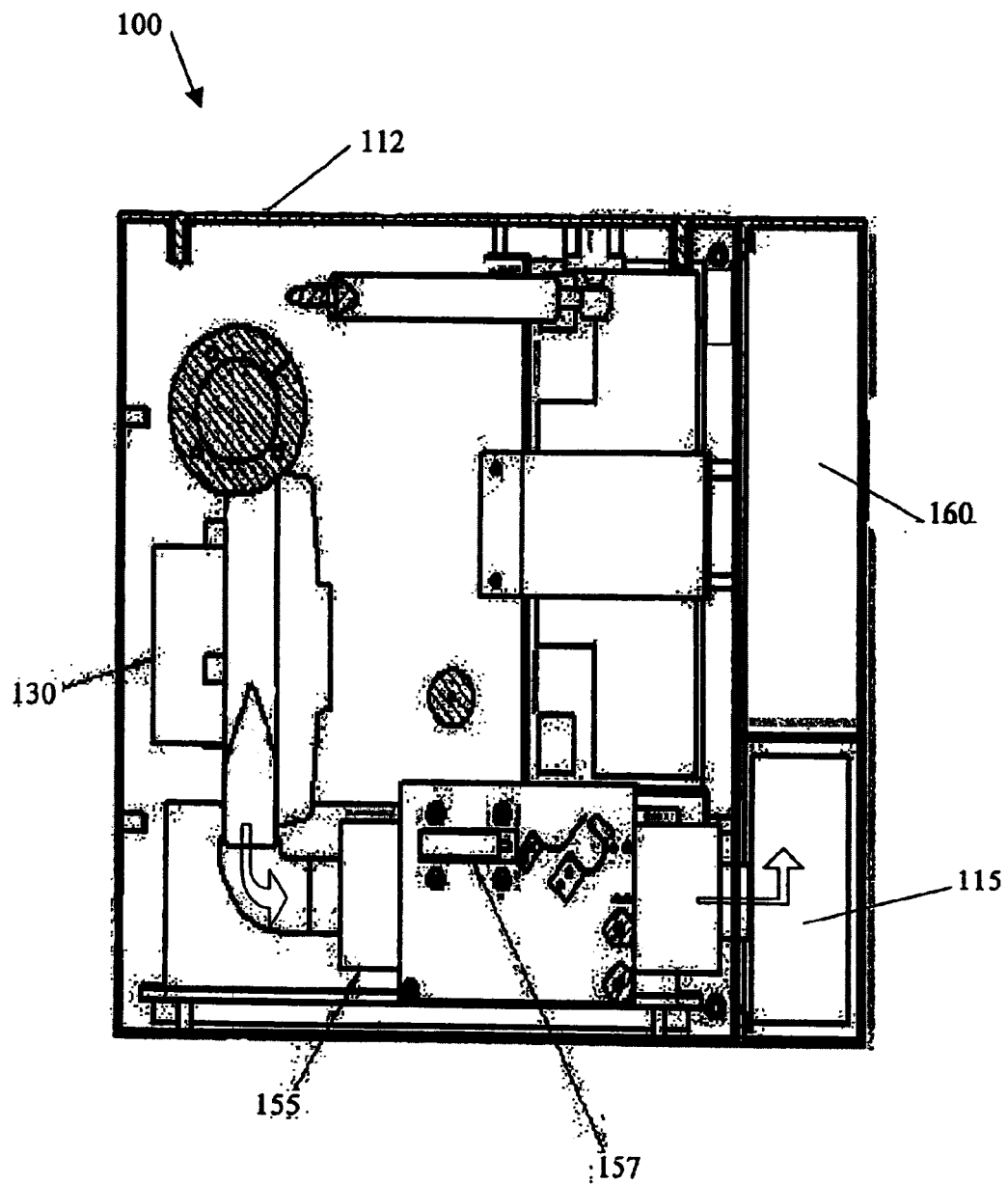
Figure 11:
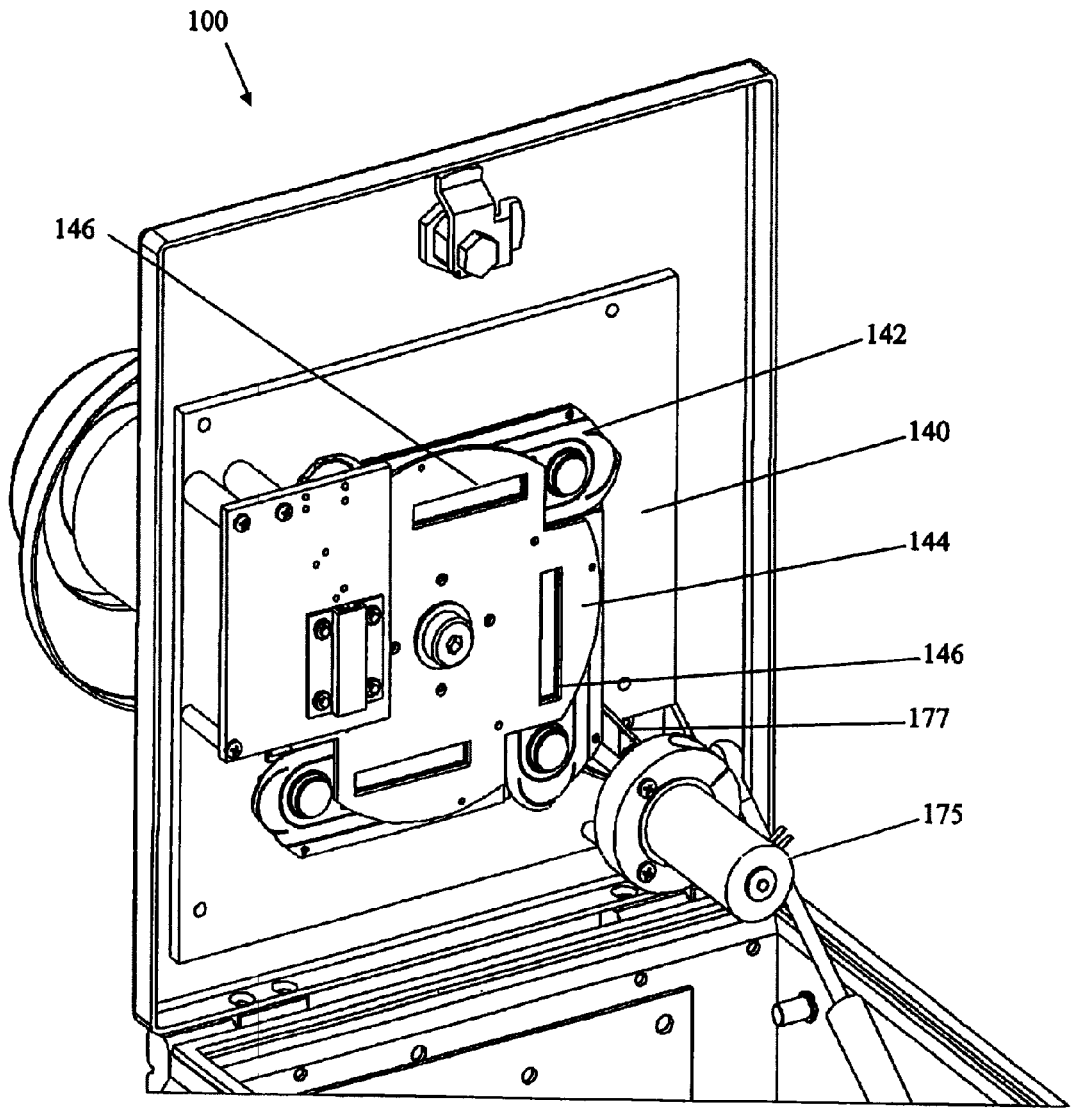

With reference to FIG. 11, collector 140 may include a holder 142, a removable carousel or rotatable case 144 which is received in holder 142, and a plurality of substrates 146 disposed in carousel 144. Holder 142 includes a nozzle (not shown) shaped as a slit for channeling the gas towards substrate 146. Further impact collectors for use in apparatus 100 of the present invention are disclosed in U.S. patent application Ser. No. 09/540,397, entitled "Impaction Substrate and Methods of Use," issued as U.S. Pat. No. 6,435,043, the entire subject matter of which is incorporated herein by reference.

With reference again to FIG. 10, apparatus 100 may include a control unit 160, such as described above in connection with apparatus 10, for monitoring and controlling the operation of apparatus 100, and transferring data between apparatus 100 and other computers via a communications network. In addition, with reference again to FIG. 11, the carousel is rotated by a servomotor 175 operably connected to the carousel via a timing belt 177. The control unit of the apparatus may control the position of each of the collectors, for example, so that sampling may occur over a continuous 24 hour time period, or periodically, e.g., every 8 or 12 hours.

The apparatus of the present invention, once set up by initializing the control unit, allows an operator to open the apparatus, exchange one or more collectors, and close the apparatus. The various collectors are desirably removable from the holders in the apparatus and placed in a tube, container or other transport device having, for example, a sealable end or ends to inhibit exposure to an operator, contamination by the operator, and contamination during transport prior to analysis. In addition, the portability of the sampling apparatus allows readily deploying a plurality of sampling apparatus over an area such as around an event in which a large number of people are gathered.

Thus, while various embodiments of the present invention have been illustrated and described, it will be appreciated to those skilled in the art that many changes and modifications may be made thereunto without departing from the spirit and scope of the invention.

What is claimed is:

1. A high-flow rate, low-noise, gas sampling apparatus for collecting particulate from a gas, said apparatus comprising:
    a housing;
    an impaction collector; and
    a device disposed within said housing for drawing the gas into said housing and exhausting the gas from said housing, said device operable to produce a flow of gas through said housing and past said collector for sampling of greater than about 50 liters per minute with a noise level emitted from said apparatus of less than about 60 decibels.

2. The apparatus of claim 1 wherein said device for drawing the gas is operable to produce the flow of gas through said housing of greater than about 100 liters per minute.

3. The apparatus of claim 1 wherein said device for drawing the gas is operable to produce the flow of gas through said housing of greater than about 200 liters per minute.

4. The apparatus of claim 1 wherein said device for drawing the gas is operable to result in a noise level emitted from said apparatus of less than about 55 decibels.

5. The apparatus of claim 1 wherein said device for drawing the gas comprises a fan.

6. The apparatus of claim 1 further comprising sound reducing material disposed on said housing.

7. The apparatus of claim 1 further comprising a muffler for reducing sound from the gas exhausted from said housing.

8. The apparatus of claim 1 further comprising a holder for receiving a biological collector.

9. The apparatus of claim 1 further comprising a holder for receiving said impaction collector.

10. The apparatus of claim 1 further comprising a movable holder for receiving a plurality of collectors.

11. The apparatus of claim 1 further comprising a radioactivity sensor for detecting presence of radioactive material on the collector.

12. The apparatus of claim 1 further comprising a holder for receiving a combination biological collector and radioactivity sensor.

13. The apparatus of claim 1 further comprising a processor for monitoring the sampling.

14. The apparatus of claim 13 further comprising a holder for receiving a combination collector and memory, said holder operably connected to said processor.

15. The apparatus of claim 13 further comprising a communications interface for connecting said processor to a communications network.

16. The apparatus of claim 1 wherein said apparatus is portable.

17. The apparatus of claim 16 further comprising a battery for powering said device.

18. A high-flow rate, low-noise, gas sampling apparatus for collecting particulate from a gas on a collector and detecting presence of radioactive material, said apparatus comprising:
    a housing;
    an impaction collector;
    a device disposed within said housing for drawing the gas into said housing and exhausting the gas from said housing, said device operable to produce a flow of gas through said housing and past said collector for sampling of greater than about 50 liters per minute with a noise level emitted from said apparatus of less than about 60 decibels;
    a radioactivity sensor for detecting the presence of radioactive material on the collector;
    a processor for monitoring the sampling; and
    a communications interface for connecting said processor to a communications network.

19. The apparatus of claim 18 wherein said device for drawing the gas comprises a fan.

20. A method for collecting particulate from a gas, the method comprising:
    drawing the gas into a housing;
    collecting, in the housing, particulate on an impaction collector for sampling;
    discharging the gas from the housing; and
    wherein a flow rate of the gas through the housing and past the impaction collector is greater than about 50 liters per minute with a noise level emitted from the housing being less than about 60 decibels.

21. The method of claim 20 wherein the flow rate through the housing is greater than about 100 liters per minute.

22. The method of claim 20 wherein the flow rate through the housing is greater than about 200 liters per minute.

23. The method of claim 20 wherein the noise level emitted from the gas sampling apparatus is less than about 55 decibels.

24. The method of claim 20 wherein the collecting particulate comprises collecting biological particulate.

25. The method of claim 20 wherein the drawing the gas comprises drawing the gas with a fan.

26. The method of claim 20 further comprising analyzing biological particulate collected on the collector.

27. The method of claim 20 further comprising detecting radioactive material on the collector.

28. The method of claim 20 further comprising monitoring the sampling.

29. The method of claim 28 further comprising communicating the sampling over a communications network.

30. A method for collecting particulate from a gas and detecting presence of radioactive material, the method comprising:
    drawing the gas into a housing;
    collecting, in the housing, particulate on an impaction collector for sampling;
    detecting for the presence of radioactive material on the collector;
    discharging the gas from the housing;
    monitoring the sampling;
    communicating the sampling over a communications network; and
    wherein a flow rate of the gas through the housing and past said collector for sampling is greater than about 50 liters per minute with a noise level emitted from the housing being lees than about 60 decibels.

* * * * *

UNITED STATES PATENT AND TRADEMARK OFFICE
CERTIFICATE OF CORRECTION

PATENT NO. : 6,867,413 B2
DATED : March 15, 2005
INVENTOR(S) : Basch et al.

It is certified that error appears in the above-identified patent and that said Letters Patent is hereby corrected as shown below:

Delete the title page and substitute therefor the attached title page.

Delete Drawing Sheets 1-8 and substitute therefor the attached Drawing Sheets 1-8.

Column 8,
Line 45, delete the word "lees" and insert -- less --.

Signed and Sealed this

Fourth Day of October, 2005

JON W. DUDAS
*Director of the United States Patent and Trademark Office*

(12) United States Patent
Basch et al.

(10) Patent No.: US 6,867,413 B2
(45) Date of Patent: Mar. 15, 2005

(54) HIGH-FLOW RATE, LOW-NOISE, GAS SAMPLING APPARATUS AND METHODS FOR COLLECTING AND DETECTING PARTICULATE IN A GAS

(75) Inventors: Lauren R. Basch, East Greenbush, NY (US); William E. Rogers, Troy, NY (US); Harvey Patashnick, Voorheesville, NY (US)

(73) Assignee: Rupprecht & Patashnick Company, Inc.

( * ) Notice: Subject to any disclaimer, the term of this patent is extended or adjusted under 35 U.S.C. 154(b) by 117 days.

(21) Appl. No.: 10/177,749

(22) Filed: Jun. 21, 2002

(65) Prior Publication Data

US 2003/0234366 A1 Dec. 25, 2003

(51) Int. Cl.$^7$ .................................................. G01T 1/00
(52) U.S. Cl. ........................................ 250/255; 250/304
(58) Field of Search ............................ 250/435, 432 R, 250/304, 255

(56) References Cited

U.S. PATENT DOCUMENTS

| | | | |
|---|---|---|---|
| 3,295,359 A | 1/1967 | Peck | 73/28 |
| 3,540,261 A | 11/1970 | Scoggins | 73/28 |
| 3,657,920 A | 4/1972 | Teel et al. | 73/28 |
| 4,277,682 A | 7/1981 | Madelaine et al. | 250/380 |
| 4,795,612 A | 1/1989 | Keller | 422/64 |
| 4,951,749 A | 8/1990 | Carroll | 166/264 |
| 5,468,968 A | 11/1995 | Bailey et al. | 250/435 |
| 5,552,610 A * | 9/1996 | McIsaac et al. | 250/435 |
| 5,553,507 A | 9/1996 | Basch et al. | 73/863.01 |
| 5,646,357 A | 7/1997 | Ogden et al. | 73/863.31 |
| 5,717,147 A | 2/1998 | Basch et al. | 73/863.23 |
| 5,834,628 A * | 11/1998 | Hunter et al. | 250/255 |
| 5,898,114 A | 4/1999 | Basch et al. | 73/863.23 |
| 5,915,268 A | 6/1999 | Linker et al. | 73/23.2 |
| 6,023,982 A | 2/2000 | Basch et al. | 73/863.25 |
| 6,138,521 A | 10/2000 | Basch et al. | 73/863.25 |
| 6,167,107 A | 12/2000 | Bates | 377/10 |
| 6,192,767 B1 | 2/2001 | Fiorina | 73/863.21 |
| 6,321,609 B1 | 11/2001 | Mengel et al. | 73/863.21 |
| 6,435,043 B1 | 8/2002 | Ferguson et al. | 73/863.22 |
| 2001/0029793 A1 | 10/2001 | Moler et al. | 73/863.22 |

FOREIGN PATENT DOCUMENTS

EP 0964241 A1 12/1999

* cited by examiner

*Primary Examiner*—Constantine Hannaher
(74) *Attorney, Agent, or Firm*—Heslin Rothenberg Farley & Mesiti P.C.

(57) ABSTRACT

A high-flow rate, low-noise, gas sampling apparatus for collecting particulate such as biological, chemical, and radioactive material from a gas on a collector such as an impaction collector includes a housing having an inlet and an outlet and a fan disposed within the housing for drawing the gas into the inlet, past the collector for sampling, and exhausting the gas through the outlet. The fan is operable to produce a flow of gas through the housing of greater than about 50 liters per minute with a noise level emitted from the apparatus being less than about 60 decibels. The apparatus may be configured as a compact, unobtrusive, portable, lightweight apparatus for use in various indoor or outdoor locations. The apparatus may also include a sensor for the detection of radioactive material collected on the collector, a processor for monitoring the sampling, and the apparatus may be linked to a communications network such as the Internet. Methods for collecting particulate from a gas are also enclosed.

30 Claims, 8 Drawing Sheets

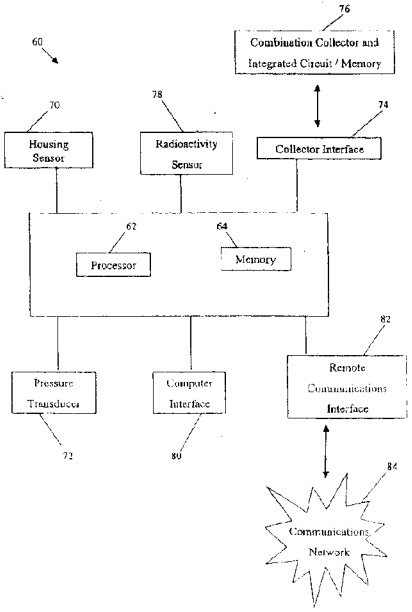

UNITED STATES PATENT AND TRADEMARK OFFICE
CERTIFICATE OF CORRECTION

PATENT NO. : 6,867,413 B2
DATED : March 15, 2005
INVENTOR(S) : Basch et al.

It is certified that error appears in the above-identified patent and that said Letters Patent is hereby corrected as shown below:

Delete Drawing Sheets 1-11 and substitute therefor the attached Drawing Sheets 1-11.

Column 8,
Line 45, delete the word "lees" and insert -- less --.

Signed and Sealed this

Sixth Day of December, 2005

JON W. DUDAS
*Director of the United States Patent and Trademark Office*